US011413079B2

(12) United States Patent
Murdoch et al.

(10) Patent No.: US 11,413,079 B2
(45) Date of Patent: Aug. 16, 2022

(54) KYPHOPLASTY SYSTEM AND METHOD

(71) Applicant: Osteon Medical LLC, Grand Island, NE (US)

(72) Inventors: Nathan William Murdoch, Grand Island, NE (US); Cody L. Evans, Grand Island, NE (US)

(73) Assignee: Osteon Medical LLC, Grand Island, NE (US)

( * ) Notice: Subject to any disclaimer, the term of this patent is extended or adjusted under 35 U.S.C. 154(b) by 490 days.

(21) Appl. No.: 16/668,818

(22) Filed: Oct. 30, 2019

(65) Prior Publication Data

US 2021/0015532 A1 Jan. 21, 2021

Related U.S. Application Data

(62) Division of application No. 16/522,478, filed on Jul. 25, 2019, now Pat. No. 10,820,933.
(Continued)

(51) Int. Cl.
*A61B 17/88* (2006.01)
*A61B 17/34* (2006.01)
*A61B 10/02* (2006.01)
*A61G 13/12* (2006.01)
*A61M 39/10* (2006.01)
(Continued)

(52) U.S. Cl.
CPC ........ *A61B 17/8855* (2013.01); *A61B 10/025* (2013.01); *A61B 17/3415* (2013.01); *A61B 17/3472* (2013.01); *A61B 17/8822* (2013.01); *A61G 13/121* (2013.01); *A61M 39/10* (2013.01); *G09B 23/30* (2013.01); *A61B 17/8811* (2013.01); *A61B 17/8816* (2013.01); *A61B 17/8819* (2013.01); *A61B 90/361* (2016.02)

(58) Field of Classification Search
CPC .............. A61B 17/885; A61B 17/8852; A61B 17/8855; A61B 17/8858; A61B 17/3472
See application file for complete search history.

(56) References Cited

U.S. PATENT DOCUMENTS

| 6,127,597 A | 10/2000 | Beyar et al. |
| 6,561,724 B1 | 5/2003 | Carletti |
(Continued)

FOREIGN PATENT DOCUMENTS

WO WO 2019133775 7/2019

OTHER PUBLICATIONS

Medtronic. [Online] "Kyphon Balloon Kyphoplasty: A minimally Invasive Treatment for Spinal Fractures," Copyright 2011 [Retrieved on Aug. 7, 2019] Retrieved from Internet: URL<http://www.back.com/wcm/groups/mdtcom_sg/mdt/back/neuro/documents/documents/contrib_186028.pdf> 20 pages.
(Continued)

*Primary Examiner* — Si Ming Ku
(74) *Attorney, Agent, or Firm* — Fish & Richardson P.C.

(57) ABSTRACT

A kyphoplasty system includes various instruments which can be selectively used in a surgical theater (e.g., during a surgical operation on a patient) or a surgical training environment. The kyphoplasty system can include one or more of a kyphoplasty apparatus, a prone table mat, a connector system, a bone introducer needle, and a biopsy device. The kyphoplasty system may also include a training system for use in the training environment.

20 Claims, 22 Drawing Sheets

Related U.S. Application Data

(60) Provisional application No. 62/874,090, filed on Jul. 15, 2019.

(51) Int. Cl.
*G09B 23/30* (2006.01)
*A61B 90/00* (2016.01)

(56) References Cited

U.S. PATENT DOCUMENTS

| | | | |
|---|---|---|---|
| 6,716,216 B1 * | 4/2004 | Boucher | A61B 17/1631 606/86 R |
| 7,628,800 B2 | 12/2009 | Sherman et al. | |
| 7,666,205 B2 | 2/2010 | Weikel et al. | |
| 8,647,378 B2 | 2/2014 | Mews et al. | |
| 8,870,888 B2 | 10/2014 | Steffen et al. | |
| 8,900,304 B1 * | 12/2014 | Alobaid | A61B 17/7097 606/92 |
| 8,986,386 B2 | 3/2015 | Oglaza et al. | |
| 9,283,018 B1 | 3/2016 | Alobaid | |
| 9,414,933 B2 | 8/2016 | Banouskou | |
| 9,579,130 B2 | 2/2017 | Oglaza et al. | |
| 10,820,933 B1 | 11/2020 | Murdoch et al. | |
| 10,821,002 B1 | 11/2020 | Hibri | |
| 10,881,522 B2 | 1/2021 | Hibri | |
| 2006/0079905 A1 | 4/2006 | Beyar | |
| 2007/0293866 A1 | 12/2007 | Stoeckel et al. | |
| 2010/0198225 A1 | 8/2010 | Thompson et al. | |
| 2010/0249933 A1 | 9/2010 | Trieu | |
| 2010/0284734 A1 | 11/2010 | Turnour | |
| 2012/0259375 A1 * | 10/2012 | Druma | A61B 17/8855 606/86 R |
| 2015/0012002 A1 | 1/2015 | Steffen et al. | |
| 2018/0256188 A1 | 9/2018 | Goshayeshgar | |
| 2019/0167333 A1 | 6/2019 | Druma | |
| 2021/0015531 A1 | 1/2021 | Murdoch et al. | |
| 2021/0015533 A1 | 1/2021 | Murdoch et al. | |
| 2021/0015534 A1 | 1/2021 | Murdoch et al. | |
| 2021/0045788 A1 | 2/2021 | Murdoch et al. | |

OTHER PUBLICATIONS

Strykier. [Online] "iVAS Inflatable Vertebral Augmentation System: Procedure Overview," Copyright 2011, Brochure Available on or before Sep. 2, 2018 [Retrieved on Aug. 7, 2019] Retrieved from Internet: URL< https://pain-doc.co.uk/wp-content/uploads/2017/11/Procedure_Overview.pdf> 6 pages.

Vexim. [Online] "SpineJack: Controlled Anatomical Respiration: Introducing the surgical technique," Available on or before Jul. 15, 2019, [Retrieved on Aug. 7, 2019] Retrieved from Internet: URL<https://en.vexim.com/wp-content/uploads/sites/11/2017/03/SpineJack%C2%AE-Surgical-Technique.pdf> , 12 pages.

Cornelis et al., "Innovative spine implants for improved augmentation and stability in neoplastic vertebral compression fracture," Medicina, Aug. 2019, 55(8):426.

DePuy Synthes, "VBS-Vertebral Body Stenting System: Surgical Technique," from URL <http://synthes.vo.llnwd.net/o16/LLNWMB8/INT%20Mobile/Synthes%20International/SGT-EMEA-Agile/SE_818940AA/SE_818940AAeng.pdf>, Nov. 2020, 27 pages.

izimed.com, "Kiva VCF Treatment System: The Implant Solution for Restoration of Sagittal Alignment," from URL <https://static1.squarespace.com/static/5cba31329b8fe86db05fc0eb/t/5d922d0d7ee00f102eb54317/1569860889779/L127+KIVA+Surgeon+Brochure%2C+Rev.+B.pdf>, Sep. 9, 2019, 8 pages.

\* cited by examiner

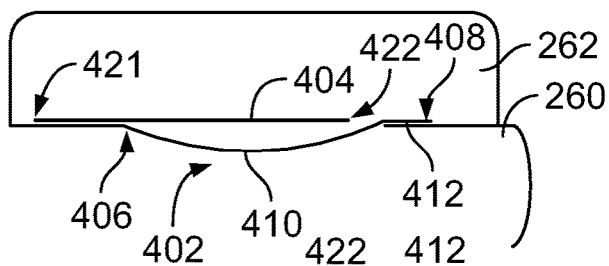
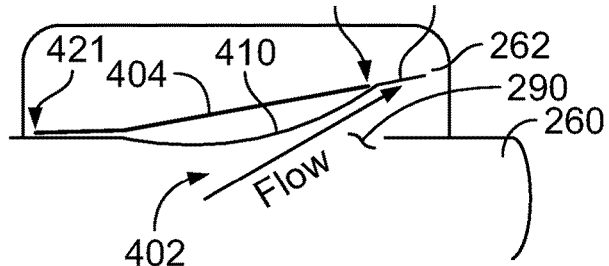
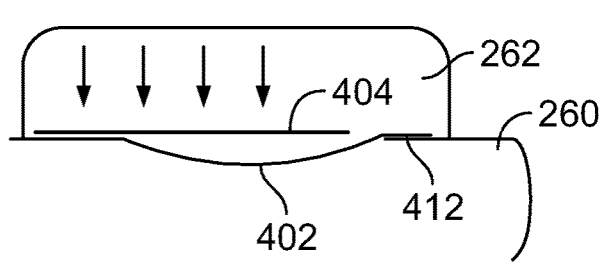
FIG. 4
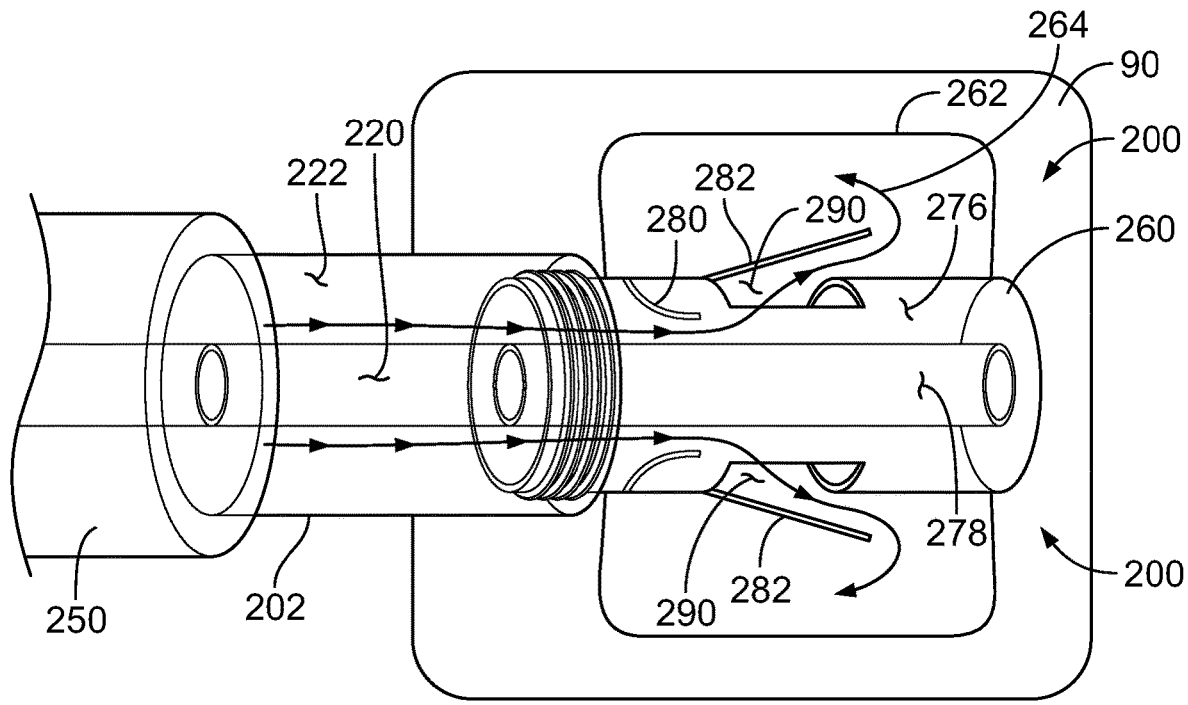
FIG. 5

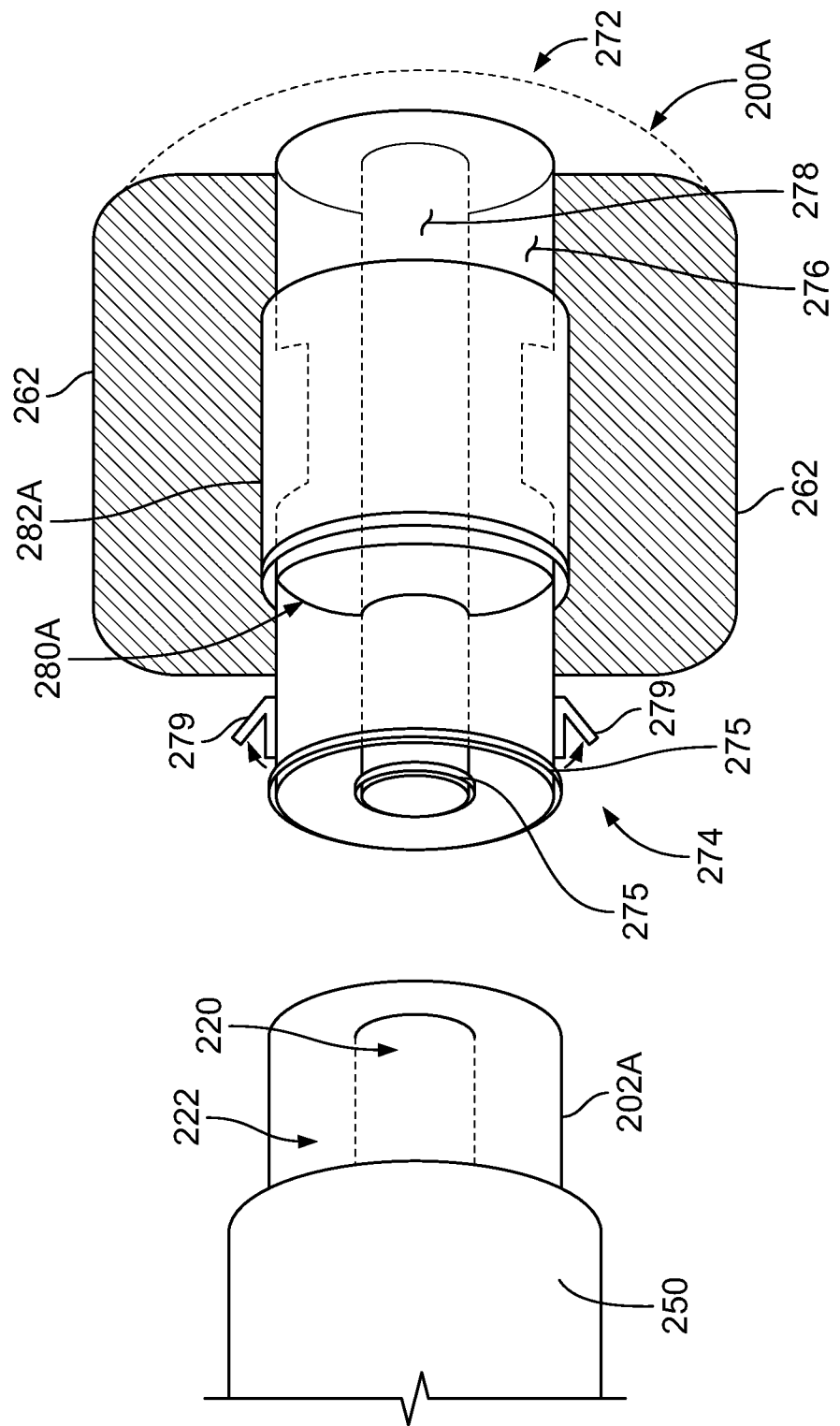

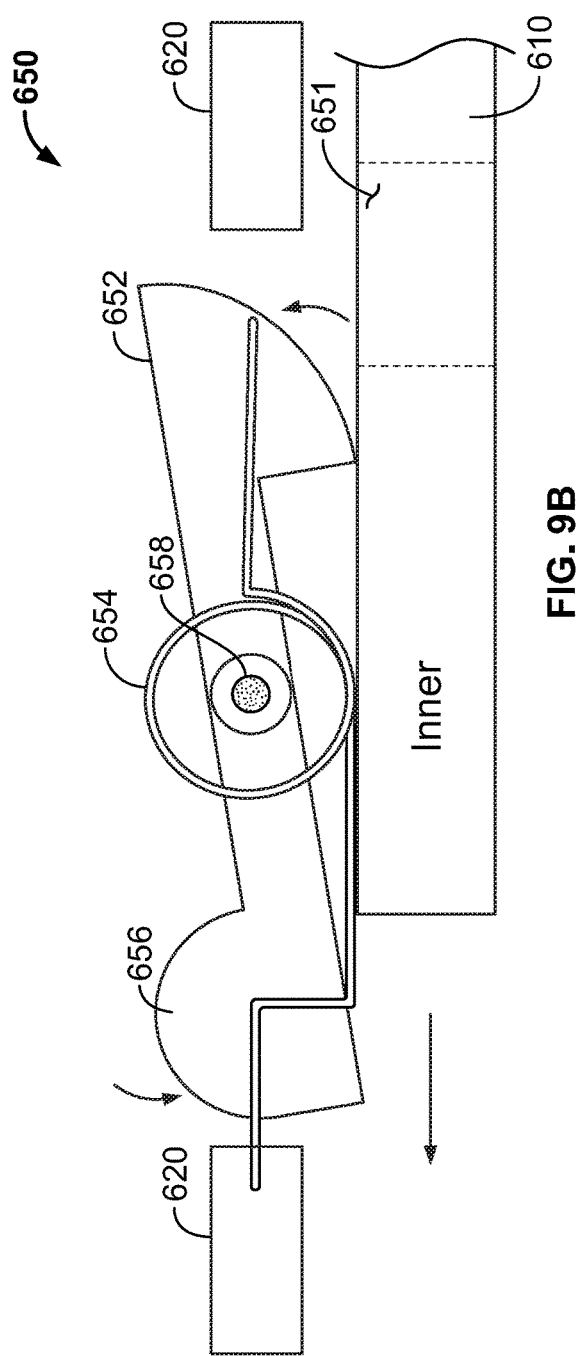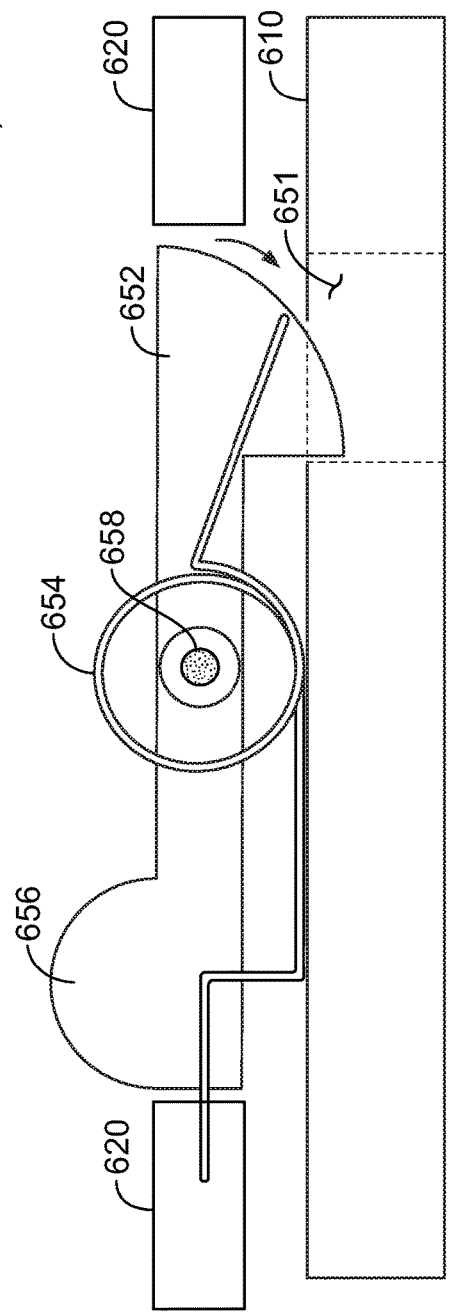

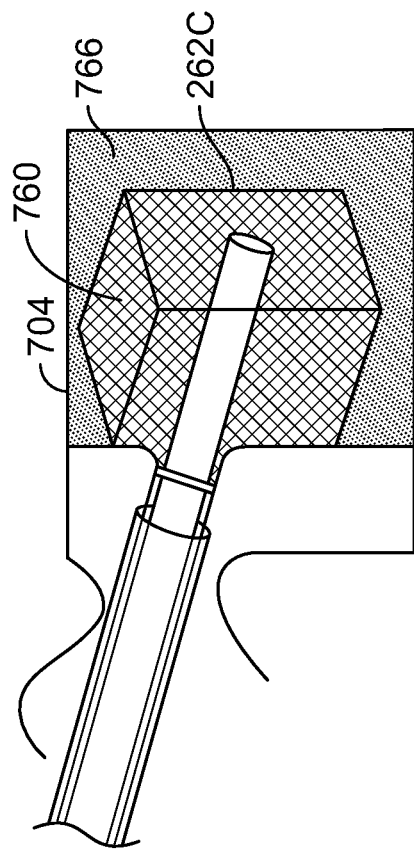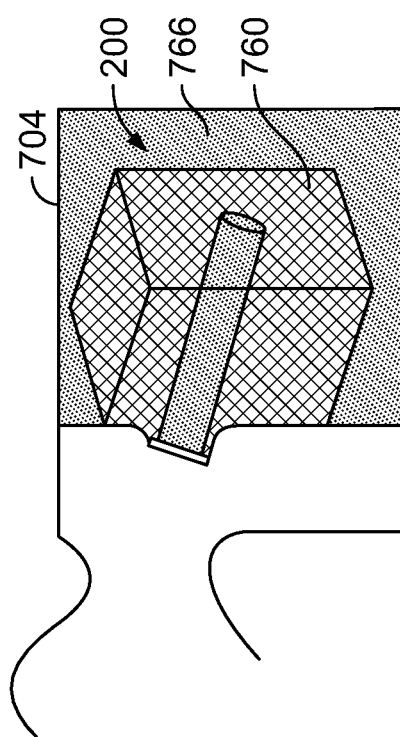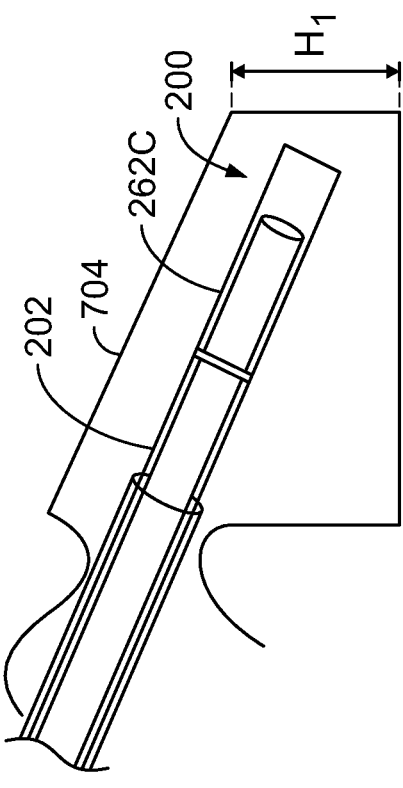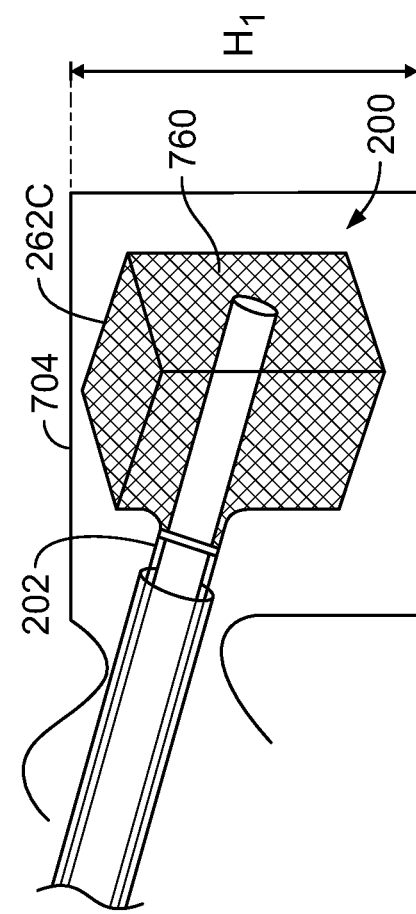

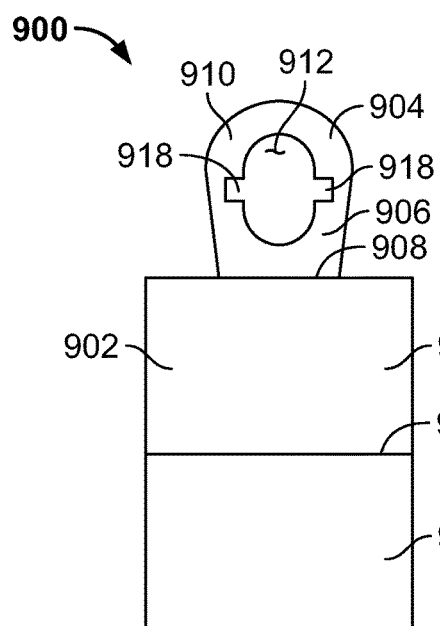
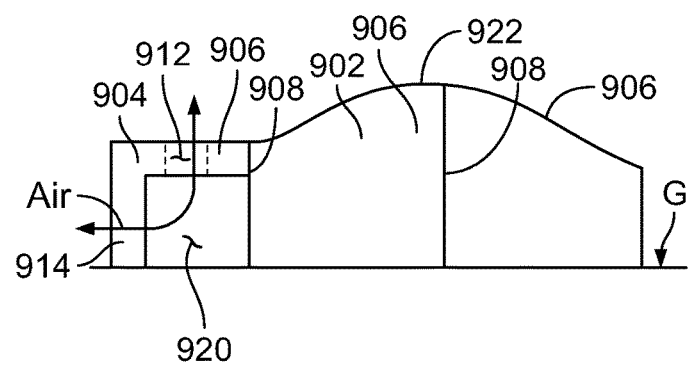
FIG. 18A                FIG. 18B
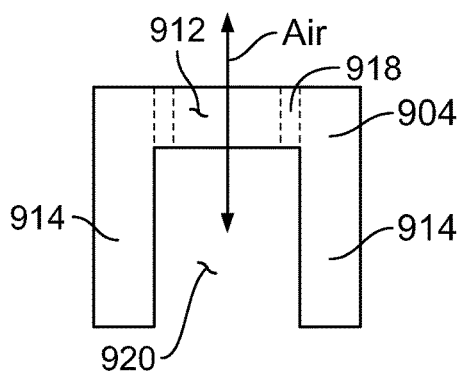
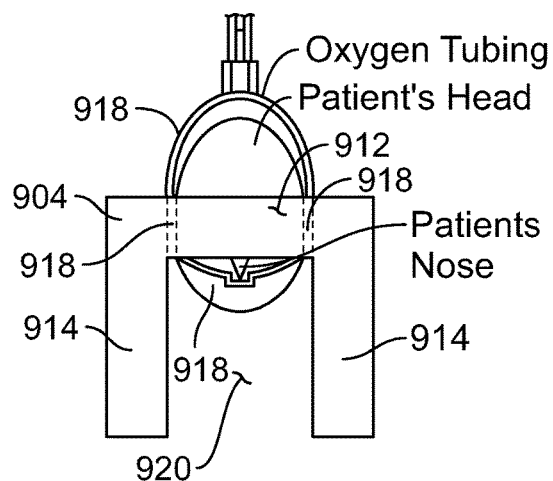
FIG. 18C                FIG. 18D

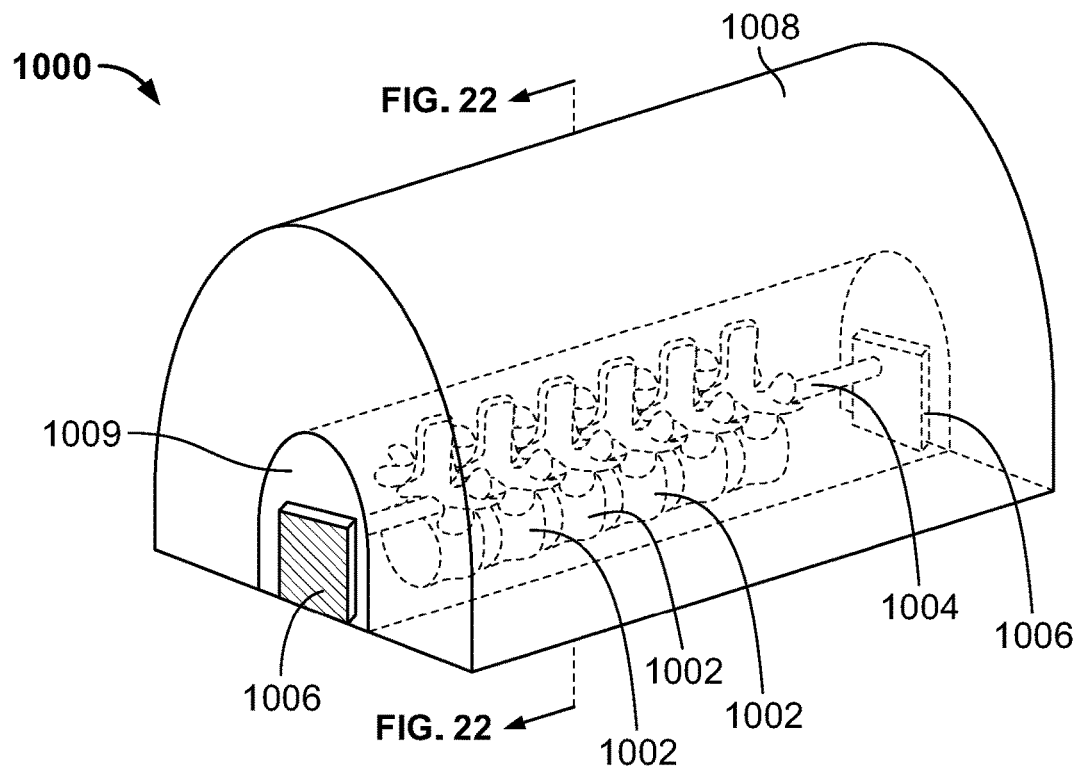
FIG. 21
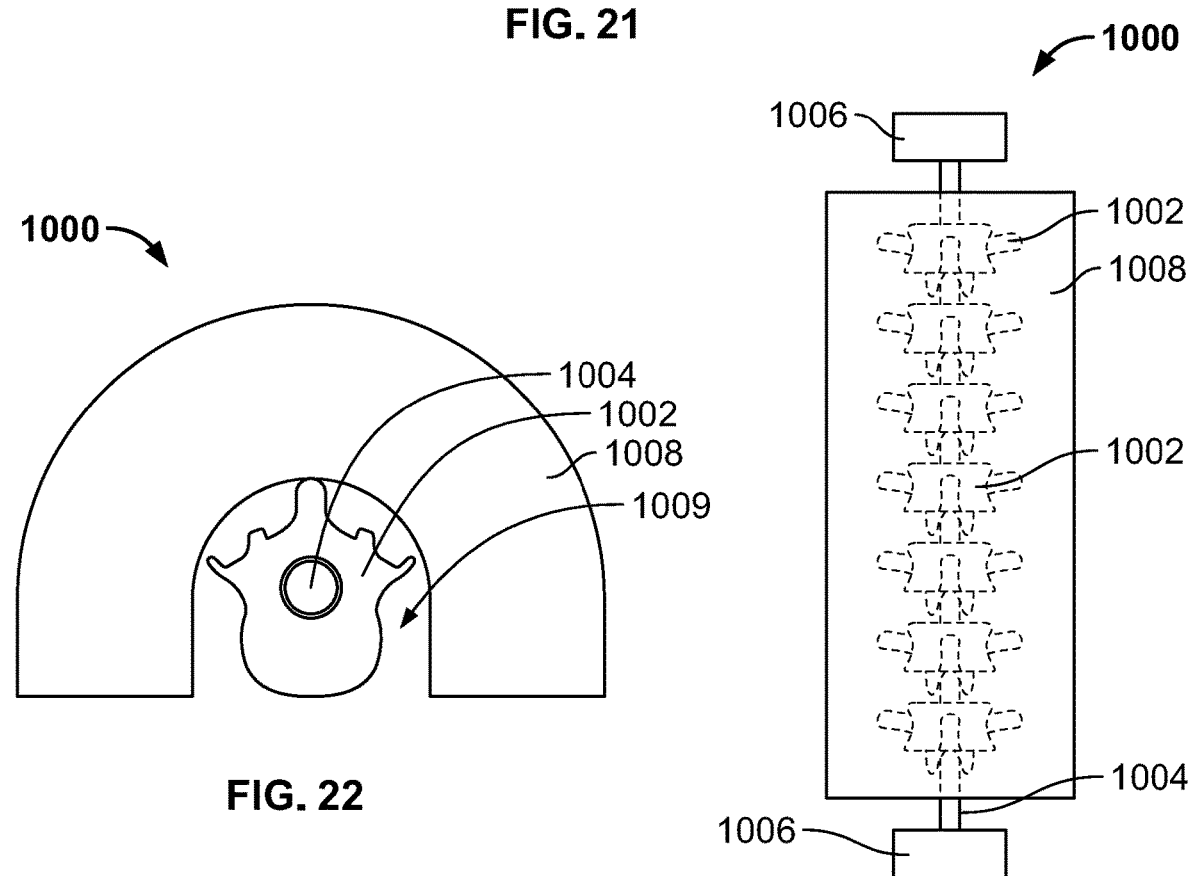
FIG. 22
FIG. 23

KYPHOPLASTY SYSTEM AND METHOD

CROSS-REFERENCE TO RELATED APPLICATION(S)

This application claims priority to U.S. application Ser. No. 16/522,478 filed on Jul. 25, 2019 (now U.S. Pat. No. 10,820,933), which claims the benefit of U.S. Provisional Application Ser. No. 62/874,090, filed on Jul. 15, 2019, the contents of these aforementioned applications being fully incorporated herein by reference.

TECHNICAL FIELD

This document generally relates to kyphoplasty or other interventional spinal procedures.

BACKGROUND

Kyphoplasty is a minimally invasive surgical procedure for treatment of pain caused by vertebral body compression fractures. Typically, the procedure involves insertion of one or more coaxial 8-10 gauge bone introducer needles under fluoroscopic guidance into one or more fractured vertebral bodies utilizing a bipedicular, unipedicular, or extrapedicular approach. In some approaches, after a bone introducer needle is in place, the inner portion of the bone introducer needle is removed and the outer portion of the bone introducer needle remains as a guide and support for the remaining procedure. Through the bone introducer needle, a drill and curette are utilized for cavity creation in the vertebral body. In many cases, after the cavity is created, the drill and curette are removed, and a deflated balloon is inserted into the cavity of the vertebral body. The balloon is then inflated, for example, by injecting a solution into the balloon, thereby expanding the drilled cavity into a desired size within the vertebral body. When the cavity is expanded to the desired size, the balloon is deflated and removed from the vertebral body. Usually in such cases, a bone filler is advanced into the vertebral body, and the expanded cavity is filled with cement.

SUMMARY

Some embodiments described herein include a kyphoplasty system. The kyphoplasty system includes a multi-functionality device that simplifies cavity creation and filling processes with improved height restoration of a fractured vertebral body. For example, the kyphoplasty system can be configured to maintain a desired anatomic height (e.g., after a balloon is inserted to expand a cavity to a desired height) before and during the delivery of cement to the expanded cavity. Further, in some examples described herein, the kyphoplasty system can employ an instrument that is configured to both expand the cavity to the desired anatomic height (e.g., using a balloon) and also fill the cavity with cement.

Embodiments of the multi-functionality device disclosed herein integrate a balloon with a bone filler device, and configured as a single unit which can be detachably coupled to a distal end of an elongated shaft of a kyphoplasty device. The multi-functionality device can be introduced into a fractured vertebral body by advancing the shaft of the kyphoplasty device mounting the multi-functionality device at the distal end, into the fractured vertebral body. The shaft with the multi-functionality device can be introduced through, for example, a bone introducer needle being inserted into the fractured vertebral body. While inserted into the vertebral body, the multi-functionality device then advantageously allows both inflating the balloon and injecting bone filling substance into the fractured vertebral body. Such balloon inflation and bone filler injection can be performed sequentially, simultaneously, or alternatingly while the multi-functionality device remains in the vertebral body.

In some examples, the multi-functionality device is a dual port device including a body and an inflatable balloon attached around the body. The body can include a first passage for delivering a balloon inflation substance into the balloon for inflation, and a second passage for delivering a bone filling substance into a compressed or fractured vertebral body. The body can be detachably coupled to a distal end of an elongate shaft of a kyphoplasty device, which can inserted through a bone introducer needle to arrange the dual port device in place within the vertebral body. The shaft can include first and second channels that can be in fluid communication with the first and second passages of the dual port device when the dual port device is mounted to the distal end of the shaft. The balloon inflation substance can be delivered through the first channel of the shaft and the first passage of the dual port device and further into the balloon. The bone filling substance can be delivered through the second channel of the shaft and the second passage of the dual port device and further into the vertebral body. For example, when the dual port device is placed within the vertebral body, the balloon inflation substance can be injected into the balloon through the first channel of the shaft and the first passage of the dual port device until the balloon is inflated to secure a desired height in the vertebral body. While the balloon remains inflated to maintain the desired height in the vertebral body, the bone filling substance can be injected into, and at least partially fill in, the vertebral body through the second channel of the shaft and the second passage of the dual port device. Once the vertebral body is filled with the bone filing substance, the shaft is decoupled from the dual port device and removed through the bone introducer needle.

In some examples, the dual port device disclosed herein includes one or more one-way valves arranged in the first passage of the dual port device and/or in an interface between the balloon and the first passage of the dual port device. The one-way valves are configured to allow flow of the balloon inflation substance into the balloon while preventing backflow in the opposite direction.

The balloon can be configured to form various inflated shapes, such as spheres, cylinders, cubes, diamonds, prisms, and other multifaceted 3-D shapes. For example, multifaceted shapes, such as diamond shapes, can increase surface area contact. In addition or alternatively, the kyphoplasty apparatus can include multiple sets of shafts and dual port devices that are operated simultaneously or in sequence.

Some embodiments of the technologies described herein include a connection system that allows compact, easy, and reliable engagement between instruments in the kyphoplasty system or other interventional procedures. For example, the connection system can be sized sufficiently small and provide minimum interference between different sets of instruments that are arranged together in a dense area where many instruments are introduced into the patient. That way, multiple instruments may be used in a small area of the patient body at the same time while also reducing obstructions in the working space located exterior to the patient. For example, the kyphoplasty system in some embodiments herein may use a plurality of bone introducer needles to access a plurality of vertebral bodies that are closely arranged, and each bone introducer needle may include a needle (e.g., a cannula) and a head (e.g., an inner connector) fixed to an end of the needle. The head of the bone introducer needle can be releasably coupled (e.g., snap-fit) to an exterior connector so that a user (e.g., a physician) may grasp the exterior connector to push the bone introducer needle into a vertebral body or insert other instruments through the bone introducer needle by engaging the exterior connector mounting such other instruments with the head of the bone introducer needle. Once the bone introducer needle is in place or such other instruments are arranged through the bone introducer needle, the exterior connector can be removed from the head of the bone introducer needle. Preferably, the head of the bone introducer needle and/or each exterior connector are sized sufficiently small and provide minimum interference between different sets of instruments that are arranged together in a dense area where many instruments are introduced into the patient.

Embodiments of the connection system disclosed herein includes a first connector mounted to a first component, and a second connector mounted to a second component. In some examples, the first component may include a bone introducer needle, a biopsy needle, other types of needles, cannulas, drill tips, a kyphoplasty apparatus (e.g., the shaft mounting the multi-functionality device), and other suitable instruments for kyphoplasty. The second connector can be connected to a tool for controlling the second component. For example, the second connector is fixed to, or integrally formed with, a tool. Alternatively, the second connector can be removably engaged with a coupling feature (e.g., a socket) of a tool. Such a tool can include a manual handle grip, a manual or electrical drill, and other suitable manual or electrical tools. In some examples, the first connector (e.g., an inner connector) is at least partially received within the second connector (e.g., an outer connector), and releasably coupled with the second connector. The first and second connectors are shaped to prevent the first component from radially moving relative to the second component. The connection system can further includes a spring clasp that prevents an axial movement of the first connector relative to the second connector. The first and second connectors can be configured to have small form factors that provide sufficient spacing between adjacent components when the components are introduced into the patient and/or arranged in place.

In particular embodiments, the spring clasp of the connection system can be configured to allow the second connector (e.g., an outer connector) to connect with the first connector (e.g., an inner connector) by simply inserting the first connector to the second connector. For example, the spring clasp is pivotally arranged in the second connector and includes a hook portion. The spring clasp is biased to a hooked position. As the first connector is inserted into the second connector, the first connector engages with the spring clasp of the second connector and pivots the spring clasp against the biasing force until the spring clasp returns to the hooked position where the hook portion of the spring clasp snaps in a corresponding notch defined on the first connector. In addition or alternatively, the spring clasp can be configured to release the first connector from the second connector by simply pushing a portion of the spring clasp away from the hooked position.

Embodiments of the connection system disclosed herein include an instrument length extension device for the connection system. The instrument length extension device is configured to extend a length of an instrument used in kyphoplasty. In some examples, the instrument length extension device includes an extension shaft having a first end and an opposite second end. The first end of the extension shaft mounts a first extension connector, and the second end of the extension shaft mounts a second extension connector. The first extension connector is configured similar to the first connector (e.g., an inner connector) of the connection system and engageable with the second connector (e.g., an outer connector) of the connection system. The second extension connector is configured similar to the second connector (e.g., the outer connector) of the connection system and engageable with the first connector (e.g., the inner connector) of the connection system. The instrument length extension device can effectively extend a length of the first component (e.g., a needle) by simply coupling the second extension connector of the extension device to the first connector of the first component, and by simply coupling the first extension connector of the extension device to the second connector connected (e.g., fixed or removably engaged) to a tool (e.g., a handle grip or drill).

Embodiments of the connection system disclosed herein include an instrument spacer configured as a sleeve with a predetermined axial length. The instrument spacer can be slid around an instrument (e.g., a bone biopsy needle, a drill bit, etc.) before the instrument is inserted into a bone introducer needle. The instrument spacer can be slidably positioned around the instrument and arranged between the first connector (e.g., an inner connector) of the bone introducer needle and the second connector (e.g., an outer connector) coupled to a tool (e.g., a drill handle). As the instrument (e.g., a bone biopsy needle or a drill shaft) moves toward a vertebral body, the instrument spacer can stop the instrument from moving further axially by engaging with the first connector of the bone introducer needle at one axial end and with the second connector coupled to the tool at the opposite axial end.

Some embodiments of the technologies described herein include a prone mat that allows a patient to comfortably lie flat and prone during kyphoplasty and other procedures which require patients to remain in a prone position. The prone mat is configured to be lightweight and portable so as to be easily transportable between different rooms and placed on any type of existing tables and beds. In addition, the prone mat can be configured to be foldable to reduce its size for convenient transportation.

Embodiments of the prone mat disclosed herein include a body portion and a head portion connected to the body portion. The body portion is configured to support at least a portion of a patient's trunk (e.g., torso). In addition, the body portion can be configured to further support lower limbs (e.g., legs). The head portion extends from the body portion and is configured to support a patient's head. The head portion includes a rim portion that at least partially defines an opening for exposing at least a portion of the patient's face (including eyes, nose, and mouth) while supporting the patient's head when the patient lies in a face-down position. The head portion includes a vertical support portion configured to position the rim portion away from a bottom level where the body portion is seated, and thus provide a space between the rim portion and the bottom level so that the patient's face does not touch the bottom level and is sufficiently raised from the bottom level. In addition, the head portion includes one or more tube notches configured to route one or more tubes (e.g., oxygen tubes) around the patient's head during procedures.

Some embodiments of the technologies described herein include an introducer needle with a backflow prevention device. Embodiments of the backflow prevention device of the introducer needle include a one-way valve arranged in a hub of the introducer needle. For example, the introducer needle includes a needle and a hub mounted at an end of the needle. The hub defines an interior space being in fluid communication with a canal of the needle, and further includes a one-way valve arranged within the interior space and configured to prevent backflow of blood or body fluids (e.g., flow in a direction away from a patient's body) when, for example, a biopsy needle is removed from the patient's body through the introducer needle. In addition, the hub can provides a coupling mechanism (e.g., a luer lock) for an instrument (e.g., a coaxial biopsy device).

Also, some embodiments of the technologies described herein includes a biopsy device (e.g., biopsy gun) configured to be coupled with an introducer needle without an additional locking device. In some examples, the introducer needle includes a hub with a first luer lock connector (e.g., a female luer lock connector), and the biopsy device includes a device body integrating a second luer lock connector (e.g., a male luer lock connector). As the biopsy device is at least partially inserted into the hub of the introducer needle, the second luer lock connector of the biopsy device can be engaged with the first luer lock connector of the hub, so that the device body of the biopsy device is secured to the hub of the introducer needle without a separate luer lock ring.

Optionally, the technologies described herein can include a radiation-free interventional spinal training system for kyphoplasty and other interventional procedures. Embodiments of the training system include one or more individual vertebral body models made of a transparent material that is penetrable by needles. For example, transparent vertebral body models can visualize kyphoplasty needles, balloons, and bone filling substances inside the models. In addition or alternatively, the vertebral body models can be configured to make an outside part (e.g., crust) harder than an inside part, thereby simulating tactile experience of touching needles to spinal bones. In addition or alternatively, the vertebral body models include markers (e.g., lines, dots, circles, etc.) indicative of educational anatomic landmarks to facilitate correct needle placement.

Additionally or alternatively, the training system includes a spinal canal model which can be made of a solid rod. The spinal canal model is configured to connect a series of vertebral body models. The vertebral body models can be individually engaged with and removed from the spinal canal model. Each of the vertebral body models can be replaced if damaged during simulated procedure. The spinal canal model can be configured to rest on a table top. The spinal canal model can be made of a transparent material to allow visualization of bone needles inside a vertebral bone.

Additionally or alternatively, the training system includes a patient body model that simulates a patient body. The patient body model can be made of a transparent material (e.g., silicon) to allow visualization of needles approaching the vertebral body models. The patient body model is configured to fit over the spinal canal model engaging one or more vertebral body models, and rest on the rest top on which the spinal canal model also rests. The patient body model can be made of a material that provides tactile simulation of advancing needles through paraspinal soft tissues.

Additionally or alternatively, the training system includes a camera support structure that simulates a C-arm machine of kyphoplasty. The camera support structure is configured to movably support a camera with respect to the patient body model and/or the spinal canal model engaging with the vertebral body models. The camera support structure can include an arc rail frame extending around the patient body model and slidably engaging with a camera bracket for mounting a camera capable of capturing videos and/or still images. Examples of such a camera include a digital camera, a mobile device (e.g., a smartphone, a tablet, etc.) including a digital camera, and other image capturing devices. The camera bracket is configured to be mounted to the arc rail frame and slide along the arc rail frame above the patient body model while capturing a video or images of training procedures with the patient body model, the spinal canal model, and/or the vertebral body models. The video or images taken by the camera can be transmitted to a display device (e.g., a display screen or monitor) and displayed on the display device so that users (e.g., trainers and trainees) can watch the procedures in real-time as they perform the procedures, just as physicians can monitor a surgical site (e.g., the inside of a vertebral body) through a C-arm system (including a display screen) during the procedure.

In addition or alternatively, the arc rail frame of the camera support structure is configured to be pivotable in a cranial-caudal plane, just as a C-arm system is maneuvered during interventional spine procedures. In addition or alternatively, the camera support structure is configured to be movable along a cranial-caudal direction. The camera support structure can be configured to be manually and/or remotely controlled to move in different planes of movement.

Particular embodiments described herein include a kyphoplasty apparatus. The apparatus includes a multi-functionality head and an elongate shaft. The multi-functionality head includes a body including a first conduit and a second conduit, and an inflatable balloon device attached to the body and configured to be in fluid communication with the first conduit of the body. The elongate shaft has a distal end and a proximate end. The shaft is configured to detachably attach the body of the multi-functionality head at the distal end. The shaft includes a bone filler channel and a balloon fluid channel. The bone filler channel is configured to be in fluid communication with the second conduit of the multi-functionality head and deliver a bone filler into a vertebral body through the second conduit. The balloon fluid channel is configured to be in fluid communication with the first conduit of the multi-functionality head and deliver a balloon fluid into the balloon device through the first conduit to inflate the balloon device within the vertebral body.

In some implementations, the system can optionally include one or more of the following features. The body may be configured to snap-fit the distal end of the shaft. The body may include a thread portion configured to be screwed to the distal end of the shaft. The second conduit may extend through a length of the body, and the first conduit is arranged around the second conduit. The balloon device may be attached to an exterior surface of the body. The balloon fluid channel may be arranged around the bone filler channel. The proximate end of the shaft may be configured to fluidly connect to a bone filler source and a balloon fluid source. The bone filler source may be configured to be in fluid communication with the bone filler channel. The balloon fluid source may be configured to be in fluid communication with the balloon fluid channel. The multi-functionality head may further include a first valve disposed in the first conduit and configured to prevent a backflow of the balloon fluid. The first valve may be a conical one-way valve. The multi-functionality head may further include a balloon port configured to make fluid communication between the first conduit and the balloon device, and a second valve configured to selectively open and close the balloon port and prevent a backflow of the balloon fluid through the balloon port. The second valve may include at least one of a one-way flap valve or a one-way sleeve valve.

Particular embodiments described herein include a method for a kyphoplasty procedure. The method includes inserting a multi-functionality head into a vertebral body, the multi-functionality head connected to a shaft; inflating a balloon device of the multi-functionality head by delivering a balloon fluid to the balloon device through a balloon fluid channel of the shaft and a first conduit of the multi-functionality head; injecting a bone filler to the vertebral body through a bone filler channel of the shaft and a second conduit of the multi-functionality head; disconnecting the shaft from the multi-functionality head; and removing the shaft from the vertebral body.

In some implementations, the system can optionally include one or more of the following features. The method may further include, prior to inserting the multi-functionality head into the vertebral body, inserting a bone introducer needle into the vertebral body, wherein the multi-functionality head is inserted into the vertebral body through the bone introducer needle. The method may further include, prior to inserting the multi-functionality head into the vertebral body, inserting a bone introducer needle with an inner stylette toward an anterior aspect of the vertebral body using image guidance; removing the inner stylette from the bone introducer needle; coaxially inserting the shaft coupled with the multi-functionality head into the bone introducer needle; and retracting posteriorly the bone introducer needle over the shaft with the coupled multi-functionality head such that the multi-functionality head is positioned at least partially uncovered inside the vertebral body. The method may further include inserting a bone biopsy needle into the vertebral body; controlling the bone biopsy needle to remove a bone sample; and removing the bone biopsy needle from the vertebral body. The method may further include inserting a bone drill bit into the vertebral body; controlling the bone drill bit to create a cavity in the vertebral body; and removing the bone drill bit from the vertebral body. The method may further include inserting a cavity curette into the vertebral body; controlling the cavity curette to remove debris in the cavity; and removing the cavity curette from the vertebral body. The multi-functionality head may be configured to be screwed to the shaft. The multi-functionality head may include a spring-biased footplate configured to be pressed against an inner surface of the bone introducer needle. The balloon device may be attached to an exterior surface of the body. The multi-functionality head may include a first valve disposed in the first conduit and configured to prevent a backflow of the balloon fluid. The multi-functionality head may include a balloon port configured to make fluid communication between the first conduit and the balloon device, and a second valve configured to selectively open and close the balloon port and prevent a backflow of the balloon fluid through the balloon port.

Particular embodiments described herein include a multi-functionality head for a kyphoplasty apparatus. The head includes a body and an inflatable balloon device. The body includes a coupling portion configured to be detachably attached to a shaft; a first conduit configured to be in fluid communication with a balloon fluid channel of the shaft to deliver a balloon fluid; and a second conduit configured to be in fluid communication with a bone filler channel of the shaft to deliver a bone filler into a vertebral body. The inflatable balloon device is attached to the body and configured to be in fluid communication with the first conduit of the body. The inflatable balloon device is inflated by the balloon fluid delivered into the balloon device through the first conduit of the body.

Particular embodiments described herein include a connection system for an interventional surgical procedure. The connection system may include a first connector and a second connector. The first connector includes a first body and a notch. The first body is attached to a bone introducer needle and includes an instrument passage open to a lumen of the bone introducer needle. The notch is provided in the first body. The second connector includes a second body and a spring clasp. The second body is attached to a surgical instrument (e.g., a driving tool) and includes a cavity configured to receive at least partially the first body of the first connector. The spring clasp is provided in the second body and configured to releasably engage with the notch of the first body when the second body receives the first body.

In some implementations, the system can optionally include one or more of the following features. The spring clasp may include a hook portion configured to snap in the notch of the first body of the first connector; and a spring element arranged to bias spring clasp to a hooked portion in which the hook portion snaps in the notch of the first body of the first connector when the first connector is received in the cavity of the second body. The spring clasp may include a release portion configured to release the hook portion from the notch. The spring clasp may be pivotally coupled to the second body. The release portion may be arranged opposite to the hook portion with a pivot axis of the spring clasp therebetween. The second body of the second connector may be configured to be releasably attached to a driving tool. The driving tool may be operable to control the surgical instrument. The driving tool may include a socket configured to fit the second body of the second connector. The surgical instrument may be one of a bone biopsy needle, a bone drill, and a kyphoplasty apparatus. The kyphoplasty apparatus may include a multi-functionality head and an elongate shaft. The head may include a body including a first conduit and a second conduit, and an inflatable balloon device attached to the body and configured to be in fluid communication with the first conduit of the body. The elongate shaft has a distal end and a proximate end. The shaft may be configured to detachably attach the body of the multi-functionality head at the distal end. The shaft may include a bone filler channel and a balloon fluid channel. The bone filler channel may be configured to be in fluid communication with the second conduit of the multi-functionality head and deliver a bone filler into a vertebral body through the second conduit. The balloon fluid channel may be configured to be in fluid communication with the first conduit of the multi-functionality head and deliver a balloon fluid into the balloon device through the first conduit to inflate the balloon device within the vertebral body. The connection system may further include an instrument length extension device configured to engage between the first connector and the second connector. The instrument length extension device may include an extension shaft including a channel; a first extension connector mounted to a first end of the extension shaft and configured to be at least partially inserted into the cavity of the second body of the second connector; and a second extension connector mounted to a second end of the extension shaft and configured to at least partially receive the first body of the first connector. The surgical instrument may extend through the channel of the extension shaft and the bone introducer needle when the instrument length extension device is engaged between the first connector and the second connector. The first extension connector may include a first extension body including a passage fluidly connected to the channel of the extension shaft; and a notch provided in the first extension body and configured to engage with the spring clasp of the second connector. The second extension connector may include a second extension body including a port fluidly connected to the channel of the extension shaft and further including an extension cavity configured to receive at least partially the first body of the first connector; and a spring clasp provided in the second extension body and configured to releasably engage with the notch of the first connector when the second extension body receives the first body of the first connector. The connection system may further include an instrument spacer configured to be slid around the surgical instrument between the first connector and the second connector. The instrument spacer may include a sleeve. The connection system may further include a set of instrument spacers having different axial lengths, each instrument spacer configured to be slid around the surgical instrument between the first connector and the second connector.

Particular embodiments described herein include a patient positioning mat. The mat includes a body portion and a head portion. The body portion is configured to support at least a portion of a patient's body in a prone position. The head portion is connected to the body portion and includes a rim portion supporting a patient's head and defining an opening for exposing a patient's face in the prone position, and a support portion configured to provide a space between the rim position and a surface on which the body portion is set.

In some implementations, the system can optionally include one or more of the following features. The head portion may include a tube notch provided in the rim portion and configured to route a tube around the patient's head. The body portion and the head portion may be foldable.

Particular embodiments described herein include an introducer needle including a needle having a canal; a hub connected to the needle and providing an interior space being in fluid communication with the canal of the needle; and a valve arranged within the interior space of the hub and configured to prevent a backflow of a fluid from a patient's body Particular embodiments described herein include a biopsy device including a biopsy needle, and a biopsy gun coupled to the biopsy needle and including a first luer lock connector. The first connector is configured to engage with a second connector provided in a bone introducer needle to releasably secure the biposy gun to the bone introducer needle.

In some implementations, the system can optionally include one or more of the following features. The first connector may be a male luer lock connector, and the second connector may be a female luer lock connector Particular embodiments described herein include an interventional spinal training system including a transparent vertebral body model configured to be similar to a vertebral body; a spinal canal model including a rod and a stand, the rod configured to removably engage the vertebral body model, and the stand configured to support the rod against a surface; and a transparent patient body model configured to fit over the spinal canal model engaging the vertebral body model.

In some implementations, the system can optionally include one or more of the following features. The vertebral body model may be made of a penetrable material. The patient body model may be made of a penetrable material. The vertebral body model may be made of a silicone. The patient body model may be made of a silicone. The interventional spinal training system may further include a camera support device configured to movably support an image capturing device around the patient body model. The camera support device may include a rail frame extending around the patient body model and a camera bracket slidably engaged with the rail frame and configured to mount an image capturing device. The rail frame may be shaped to be arc around the patient body model. The rail frame may be configured to be pivotable in a cranial-caudal plane. The interventional spinal training system may further include a display device configured to receive images from the image capturing device and display the images.

The apparatuses, systems, devices, and techniques described herein may provide one or more of the following advantages. Some embodiments described herein include a kyphoplasty system that uses multi-functionality device providing both balloon inflation and bone filling functionalities together in a single unit, thereby simplifying a kyphoplasty procedure. The dual port device improves height restoration of a fractured vertebral body by the balloon inflation, and permits for the vertebral body to be filled with the bone filler without losing the restored height.

Further, some embodiments described herein include a connection system for surgical instruments in a kyphoplasty procedure or other surgical procedures. The connection system includes a set of connectors that have small foam factors, thereby allowing minimum interference between different sets of instruments that are arranged together in a dense area where many instruments are introduced into the patient. Further, the connectors are configured to be mated with a simple coupling mechanism, thereby allowing easy and reliable engagement between instruments during the procedure. Some embodiments described herein include various instruments, such as bone introducer needles, that incorporate valves, thereby preventing backflow of blood or other body fluids through the instruments. Further, some embodiments described herein include various instruments that integrate locking devices configured to easily lock one instrument to another without a separate coupling device.

Moreover, some embodiments of the kyphoplasty system provide a patient positioning mat that is lightweight and portable and can be easily set up on an existing table or bed to allow a patient to comfortably lie in a prone position during kyphoplasty or other procedures.

Also, some embodiments described herein include an interventional spinal training system for kyphoplasty and other procedures. The training system can include simulated vertebral bodies, a simulated spinal canal, and a simulated patient body, so that a radiation-free environment is created for interventional training.

The details of one or more implementations are set forth in the accompanying drawings and the description below. Other features and advantages will be apparent from the description and drawings, and from the claims.

BRIEF DESCRIPTION OF THE DRAWINGS

FIG. 4 illustrates an example valve in the multi-functionality head of FIG. 3.
FIG. 5 illustrates that the multi-functionality head is inserted into a compressed or fractured vertebral body.

FIG. 7A schematically illustrates an example multi-functionality head.

FIG. 9B is a side cross sectional view of the spring clasp in a second position.

FIG. 9C is a side cross sectional view of the spring clasp in a third position.

FIG. 14A illustrates an example kyphoplasty procedure that includes a single multi-functionality head with a cubic inflated balloon.

FIG. 14B illustrates an example kyphoplasty procedure with the multi-functionality head of FIG. 14A.

FIG. 14C illustrates an example kyphoplasty procedure with the multi-functionality head of FIG. 14A.

FIG. 14D illustrates an example kyphoplasty procedure with the multi-functionality head of FIG. 14A.

FIG. 18A is a schematic top view of an example patient positioning mat.

FIG. 18B is a schematic side view of the patient positioning mat of FIG. 18A.

FIG. 18C is a schematic front view of the patient positioning mat of FIG. 18A.

FIG. 18D is a schematic front view of the patient positioning mat of FIG. 18A with a tubing arranged.

FIG. 21 is a schematic perspective view of an example interventional spinal training system.

FIG. 22 is a cross sectional view of the training system of FIG. 21.

FIG. 23 is a top view of the training system of FIG. 21.

DETAILED DESCRIPTION OF ILLUSTRATIVE EMBODIMENTS

Figure 1:
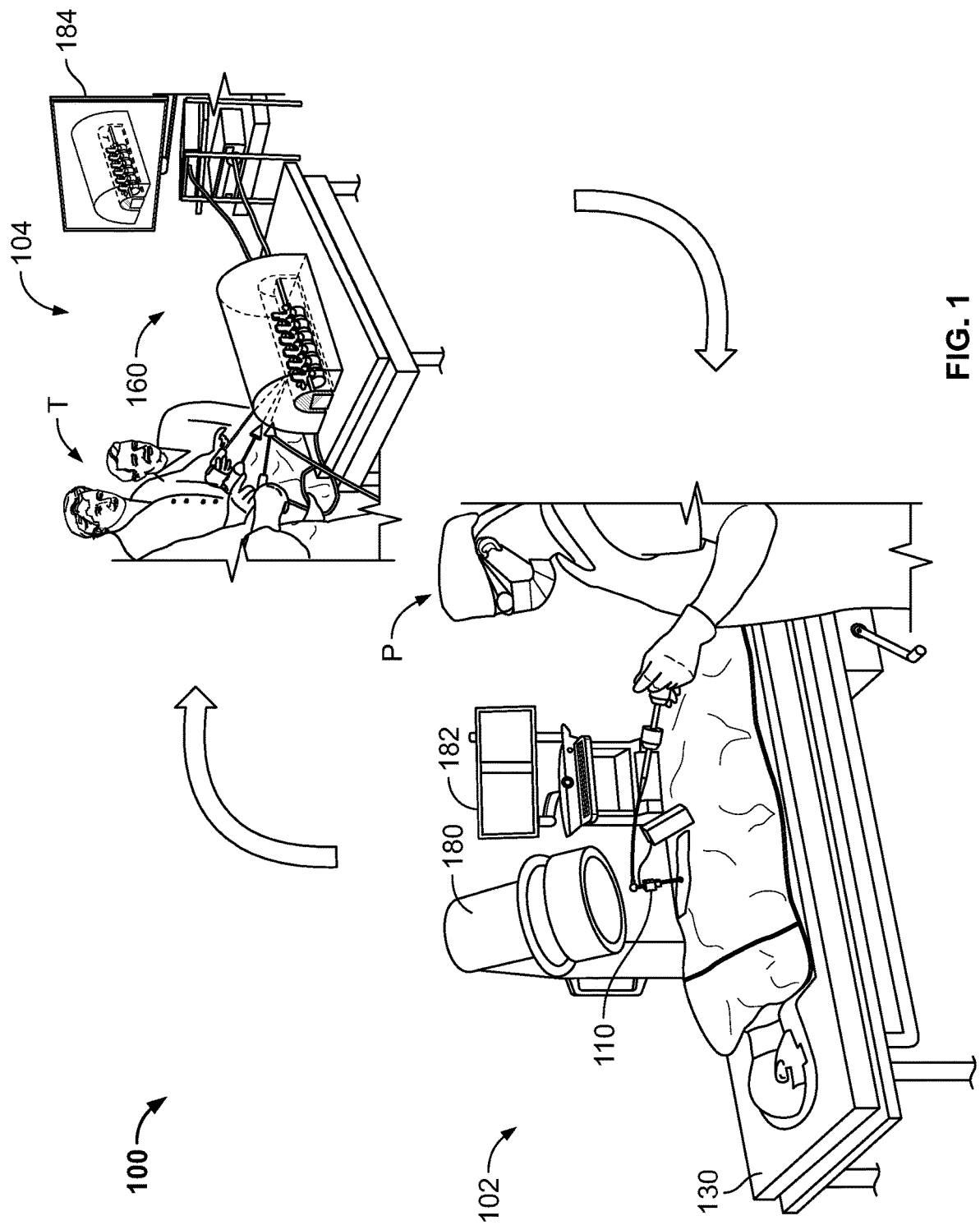
FIG. 1 illustrates an example kyphoplasty system.

FIG. 1 illustrates an example kyphoplasty system 100. The kyphoplasty system 100 includes various features which can be selectively used in a surgical theater 102 (e.g., during a surgical operation on a patient, in a surgical training environment 104, or both. For example, the kyphoplasty system 100 can include a kyphoplasty apparatus 110 and a prone table mat 130. Although not shown in FIG. 1, the kyphoplasty system 100 can further include one or more of a connector system 600 (FIGS. 8, 9A-9C, 10A-10J, 11A-11I, 16, and 17), a bone introducer needle 940 (FIG. 19A), and a biopsy device 950 (FIG. 19B), as described below. Some or all of the kyphoplasty apparatus 110, the connector system 600, the prone table mat 130, the bone introducer needle 940, and the biopsy device 950 can be selectively used in a surgical theater 102 or in a training environment 104. Optionally, the kyphoplasty system 100 can include a training system 160 for use in the training environment 104. The training system 160 can be used with or without one or more of the apparatus 110, the connector system 600, the prone table mat 130, the bone introducer needle 940, and the biopsy device 950.

In the surgical theater 102, the kypoplasty system 100 can be used with an image scanner 180, such as a C-arm machine, and a display device 182 configured to receive images (e.g., still and/or video images) from the image scanner 180 and display them to assist a practitioner (e.g., a surgeon) with the procedure.

In the training environment 104, the training system 160 is set up and permits for users (e.g., trainers and trainees) to practice kypoplasty or other interventional spinal surgical procedures. The training environment 104 may or may not be set up similarly to an operating room. The training environment 104 can include a display device 184 configured to receive images (e.g., still and/or video images) from the training system 160 and display them to assist users with the simulated procedures.

The kyphoplasty apparatus 110 includes a multi-functionality device and a shaft detachably attached to the multi-functionality device, which are configured to simplify cavity creation and filling processes with improved height restoration of a fractured vertebral body. Preferably, the kyphoplasty apparatus 110 provides a multi-functionality device that integrates a kyphoplysty balloon with a bone filler device in a single unit which can be detachably coupled to an elongated shaft of a kyphoplysty device. An example of the kyphoplasty apparatus 110 is further described herein, for example with reference to FIGS. 2-7, 11A-11I, 12A-12D, 13A-13D, 14A-14D, and 15A-15D.

The connector system 600 includes a set of connectors configured to be mated to couple separate instruments in compact, easy, and reliable configurations during procedures. The connection system 600 can include an instrument length extension device to simply extend a length of an instrument during procedures. The connection system 600 can include an instrument spacer configured to simply control a length of an instrument during procedures. An example of the connection system 600 is further described herein, for example with reference to FIGS. 8, 9A-9C, 10A-10J, 11A-11I, 16, and 17.

The prone table mat 130 can be set up on an existing table or bed and place a patient in a prone position during procedures. An example of the prone table mat 130 is further described herein, for example with reference to FIGS. 18A-18D.

The introducer needle 940 can include a backflow prevention device configured to prevent backflow of blood or body fluids through the needle. An example of the introducer needle 940 is further described herein, for example with reference to FIGS. 19A-19C.

The biopsy device 950 can be coupled with a introducer needle without an additional locking device. An example of the biopsy device 950 is further described herein, for example with reference to FIGS. 19C and 20.

The training system 160 provides a simple, radiation-free interventional spinal training system. The training system 160 can be used for kyphoplasty training or other interventional spinal procedure trainings. An example of the training system 160 is further described herein, for example with reference to FIGS. 21-24, 25A-25C, and 26A-26C.

Figure 2:
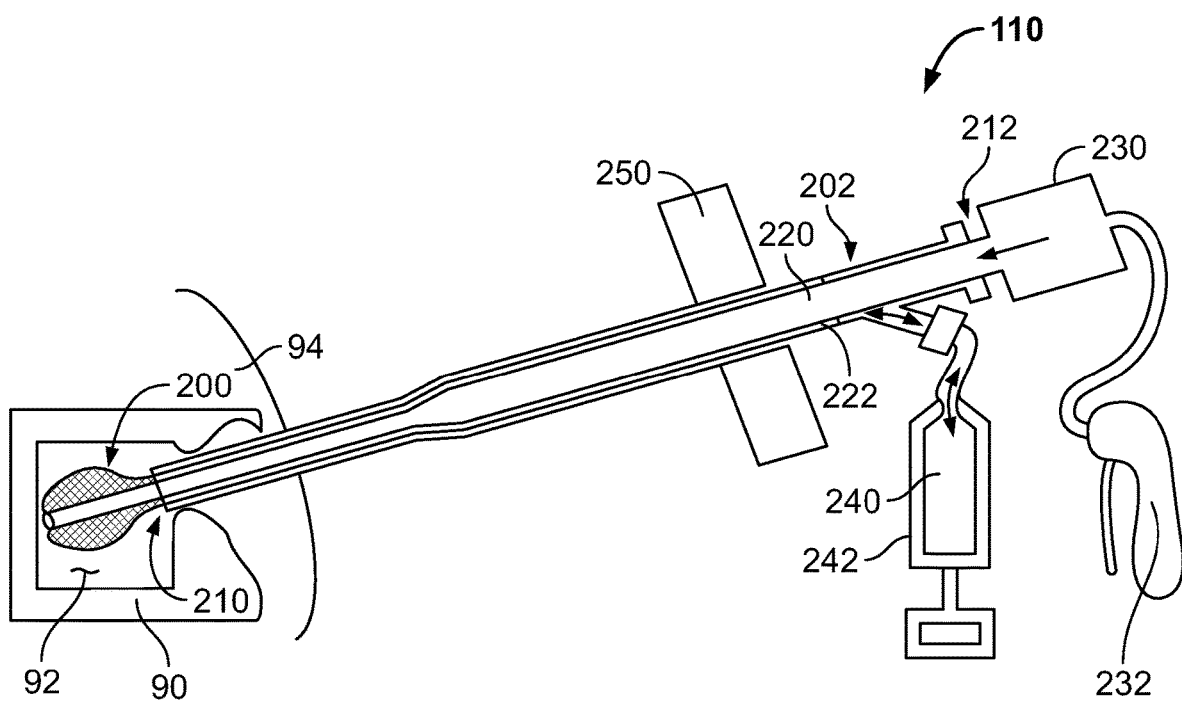
FIG. 2 schematically illustrates an example kyphoplasty apparatus.

Referring now to FIGS. 2-7 and 7A, some embodiments of the kyphoplasty apparatus 110 include a multi-functionality head 200 and an elongate shaft 202. The multi-functionality head 200 can be detachably coupled to a distal end 210 of the shaft 202. As shown in FIG. 2, the shaft 202 includes a bone filler channel 220 and a balloon fluid channel 222. The bone filler channel 220 is configured to deliver a bone filler from a filler source 230 into a cavity 92 in a vertebral body 90. For example, the bone filler channel 220 can extend at least partially along a length of the shaft 202 between the distal end 210 and an opposite proximal end 212 of the shaft 202. The bone filler channel 220 can be open at the distal end 210 of the shaft 202 so that the open end of the bone filler channel 220 can be arranged in the cavity 92 of the vertebral body 90. Further, the bone filler channel 220 can be connected to the filler source 230 at the proximal end 212 of the shaft 202. The filler source 230 contains a bone filler, such as cement, and can be connected to an actuator 232. The actuator 232 can be controlled by a user (e.g., a surgeon) to deliver the bone filler from the filler source 230 through the bone filler channel 220 of the shaft 202 in a controller manner. The actuator 232 can be of various configurations, such as a handgun that can be handled by a user to activate the delivery of the bone filler from the filler source 230.

In addition, the balloon fluid channel 222 is configured to deliver a balloon fluid from a fluid source 240 into a balloon (e.g., a balloon device 262) of the multi-functionality head 200 attached to the distal end 210 of the shaft 202. For example, the balloon fluid channel 222 can extend at least partially along the length of the shaft 202 between the distal end 210 and the proximate end 212 of the shaft 202. The balloon fluid channel 222 is configured to create fluid communication between the balloon at the distal end 210 and the fluid source 240 at the proximate end 212. The fluid source 240 contains a balloon fluid, such as saline, contrast, and/or silicone, cement (identical or similar to bone cement), or other solidifying liquid, and can be actuated by a balloon controller 242. The balloon controller 242 can be controlled by a user (e.g., a surgeon) to deliver the balloon fluid from the fluid source 240 to the balloon through the balloon fluid channel 222. The balloon controller 242 can be of various configurations, such as a syringe having a barrel containing the balloon fluid and pumped by a plunger that fits within the barrel.

In the illustrated example, the balloon fluid channel 222 is arranged at least partially around the bone filler channel 220 in the shaft 202. In other examples, the balloon fluid channel 222 and the bone filler channel 220 can be relatively arranged in other configurations, such as running parallel with each other, and/or spirally, at least partially along the length of the shaft 202.

In the illustrated example, the shaft 202 is configured to be connected to both the filler source 230 (and the actuator 232) and the fluid source 240 (and the balloon controller 242) together. In other examples, the shaft 202 is configured to be selectively connected to one of the filler source 230 (and the actuator 232) and the fluid source 240 (and the balloon controller 242). For example, the proximate end 212 of the shaft 202 is configured to be connected to the fluid source 240 (and the balloon controller 242), and then connected to the filler source 230 after the fluid source 240 is removed from the shaft 202.

A bone introducer needle 250 can be used to guide the multi-functionality head 200 and/or the shaft 202 therethrough so that they can be inserted through a patient body 94 and arranged in place within the cavity 92 of the vertebral body 90.

Figure 3:
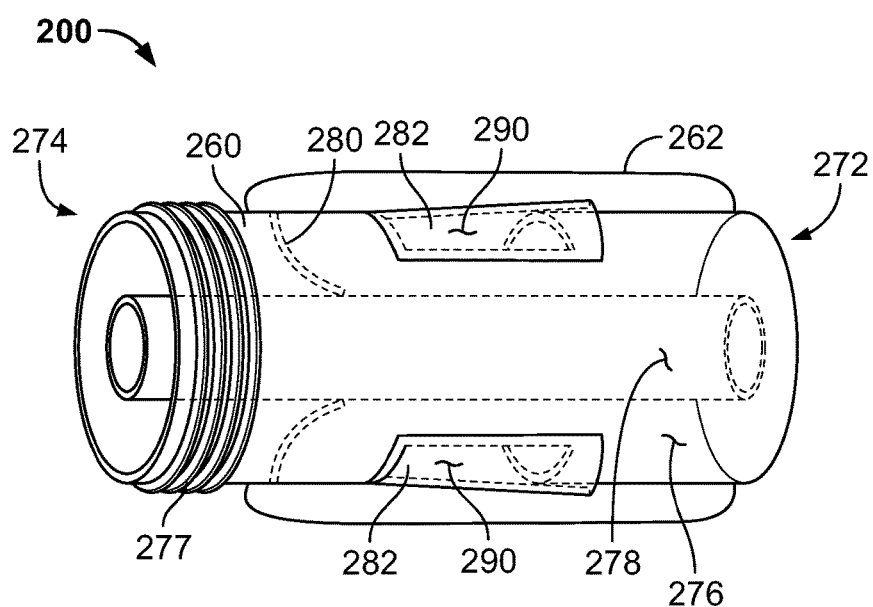
FIG. 3 schematically illustrates an example multi-functionality head.

Referring to FIG. 3, the multi-functionality head 200 includes both ballooning and bone filler functionalities that are integrated into a single unit. Optionally, some embodiments the single unit may include more ports than those illustrated in FIG. 3, but it is preferred that the single unit includes multiple ports so as to provide the dual functions of balloon expansion and bone filler insertion (as detailed below). The multi-functionality head 200 can include a body 260 and an inflatable balloon device 262 attached to the body 260.

The body 260 is configured as a cylindrical body in the illustrated example, but can be configured in other shapes in other examples. The body 260 extends between a distal body end 272 and a proximate body end 274. The proximate body end 274 of the body 260 can be configured to be detachably attached to the distal end 210 of the shaft 202. For example, the body 260 includes a threaded portion 277 at the proximate body end 274, which is configured to be engaged with the distal end 210 of the shaft 202. In the illustrated implementation, the threaded portion 277 is provided on an outer surface of the body 260, so that the proximate body end 274 of the body 260 can be screwed into the distal end 210 of the shaft 202. Alternatively, the threaded portion 277 is provided on an inner surface of the body 260 so that the proximate body end 274 of the body 260 can be threaded over the exterior of the distal end 210 of the shaft 202. The distal end 210 of the shaft 202 may have a feature (e.g., a thread) corresponding to the threaded portion 277 of the body 260 to ensure engagement between the body 260 and the shaft 202. Alternatively or in addition, the body 260 is configured to be removably connected to the distal end 210 of the shaft 202, such as using one or more spring-biased footplates 279 (FIG. 7A) or other suitable coupling or fastening mechanisms. Alternatively, the body 260 is configured to be permanently attached to the distal end 210 of the shaft 202, or made integrally with the distal end 210 of the shaft 202.

The body 260 includes a first conduit 276 and a second conduit 278 between the distal body end 272 and the proximate body end 274. The first conduit 276 is configured to be in fluid communication with the balloon fluid channel 222 of the shaft 202 when the multi-functionality head 200 is attached to the shaft 202, so that the first conduit 276 delivers the balloon fluid into the balloon device 262 for inflation. The second conduit 278 is configured to be in fluid communication with the bone filler channel 220 when the multi-functionality head 200 is attached to the shaft 202, so that the second conduit 278 delivers the bone filler into the vertebral body 90.

In the illustrated example, the second conduit 278 is provided as a hollow central canal extending along the length of the body 260, and the first conduit 276 is disposed around the second conduit 278. Other arrangements are also possible. The body 260 has various sizes. In some implementations, the body 260 ranges from 5 gauge to 20 gauge. In other implementations, the body 260 is around 12 gauge. The second conduit 278 has various sizes. In some implementations, the second conduit 278 ranges from 7 gauge to 25 gauge. In other implementations, the second conduit 278 is around 14 gauge. The first conduit 276 can be sized depending on the sizes of the body 260 and the second conduit 278. A filler needle 221 (FIG. 6) can be sized similarly to or slightly smaller than the second conduit 278. In some implementations, the filler needle 221 ranges from 7 gauge to 25 gauge. In other implementations, the filler needle 221 is around 14 gauge.

The multi-functionality head 200 can include backflow prevention features. In some implementations, the multi-functionality head 200 can include a valve system arranged and configured to allow flow of a balloon fluid into the balloon device 262 while preventing backflow in the opposite direction. For example, the multi-functionality head 200 can include a first valve 280 disposed in the first conduit 276. The first valve 280 can be arranged between the proximate body end 274 of the body 260 and a portion of the body 260 in which one or more balloon ports 290 are arranged to permit fluid communication between the first conduit 276 and the balloon device 262. The first valve 280 can be a one-way valve disposed (e.g., conically) around the second conduit 278 and configured to allow a balloon fluid to pass through from the proximate body end 274 toward the balloon ports 290 of the body 260, while preventing a backflow of the balloon fluid in the opposite direction (i.e., from the balloon ports 290 to the proximate body end 274). In addition or alternatively, the multi-functionality head 200 can include one or more second valves 282 disposed at an interface between the balloon device 262 and the first conduit 276. For example, the second valve 282 is arranged at each of the balloon ports 290 and configured to selectively open and close the balloon ports 290. The second valve 282 can be a one-way flap valve configured to permit a balloon fluid to flow from the first conduit 276 into the balloon device 262 while preventing a backflow in the opposite direction (i.e., from the balloon device 262 to the first conduit 276). Other types of one-way valves can also be used for the second valve 282, such as a one-way sleeve valve (FIG. 7A).

The balloon device 262 is attached to the body 260 and is configured to be in fluid communication with the first conduit 276 of the body 260 through one or more balloon ports 290. As described herein, the balloon ports 290 are open or closed by the second valves 282.

The balloon device 262 is initially deflated and configured to be inflated as it is filled with a balloon fluid flowing in through the balloon ports 290. The balloon fluid can be of various kinds, such as saline, silicone, cement, and other suitable fluids or semi-solid balloon injectate. The balloon device can be configured to form various inflated shapes, such as spheres, cylinders, cubes, diamonds, prisms, and other multifaceted 3-D shapes. For example, multifaceted shapes, such as diamond shapes, can increase surface area contact. Examples of such inflated shapes are illustrated and described herein, for example with reference to FIGS. 12A-12D, 13A-13D, 14A-14D, and 15A-15D.

Referring to FIG. 4, an example of the second valve 282 can include a flap 402 and a flexible element 404. The flap 402 has a fixed end 406 attached to a portion of the body 260 adjacent a balloon port 290, and a free end 408 which can freely move relative to the fixed end 406. The flap 402 has a flap body 410 extending between the fixed end 406 and the free end 408. The flap 402 includes an extension portion 412 that can seat on an exterior surface of the body 260 to close the balloon port 290. In some implementations, the flap body 410 has a curved (e.g., concave) shape that is bent toward the interior of the body 260 (and away from the balloon device 262). Such a curved flap body can help seal the balloon port 290 when the flap 402 closes the balloon port 290 by the extension portion 412 seating on the exterior surface of the body 260 (Position 1).

The flexible element 404 is configured to bias the flap 402 to a closed position where the flap 402 closes the balloon port 290, as illustrated in Position 1. The flexible element 404 is configured to provide a spring effect against the flap 402. The flexible element 404 has a fixed end 421 that is fixed at or adjacent the fixed end 406 of the flap 402, and a free end 422 that is arranged above the flap body 410 of the flap 402. The free end 422 of the flexible element 404 is configured and arranged to contact with the flap body 410 and apply a force against the flap body 410 being raised away from the balloon port 290, as illustrated in Position 2.

The second valve 282 is initially in a closed position, as illustrated in Position 1, where the flap 420 closes the balloon port 290 of the body 260 with the extension portion 412 seating on an exterior surface of the body 260. The flexible element 404 can be arranged to contact the flap 420 at least at the free end 422 so as to bias the flap 402 to the closed position.

As illustrated in Position 2, as a balloon fluid flows through the body 260 (e.g., the first conduit 276 thereof), the balloon fluid creates a forward pressure that pushes the flap 402 and the flexible element 404 away from the balloon port 290, so that the extension portion 412 of the flap 402 is raised against the biasing force of the flexible element 404, and a channel is created for the balloon fluid into the balloon device 262.

At illustrated in Position 3, when the balloon fluid fills the balloon device 262, the balloon fluid within the balloon device 262 applies a pressure against the flap 402 and/or the flexible element 404, thereby causing the flap 420 to close the balloon port 290 and prevent a backflow of the balloon fluid.

Figure 6:
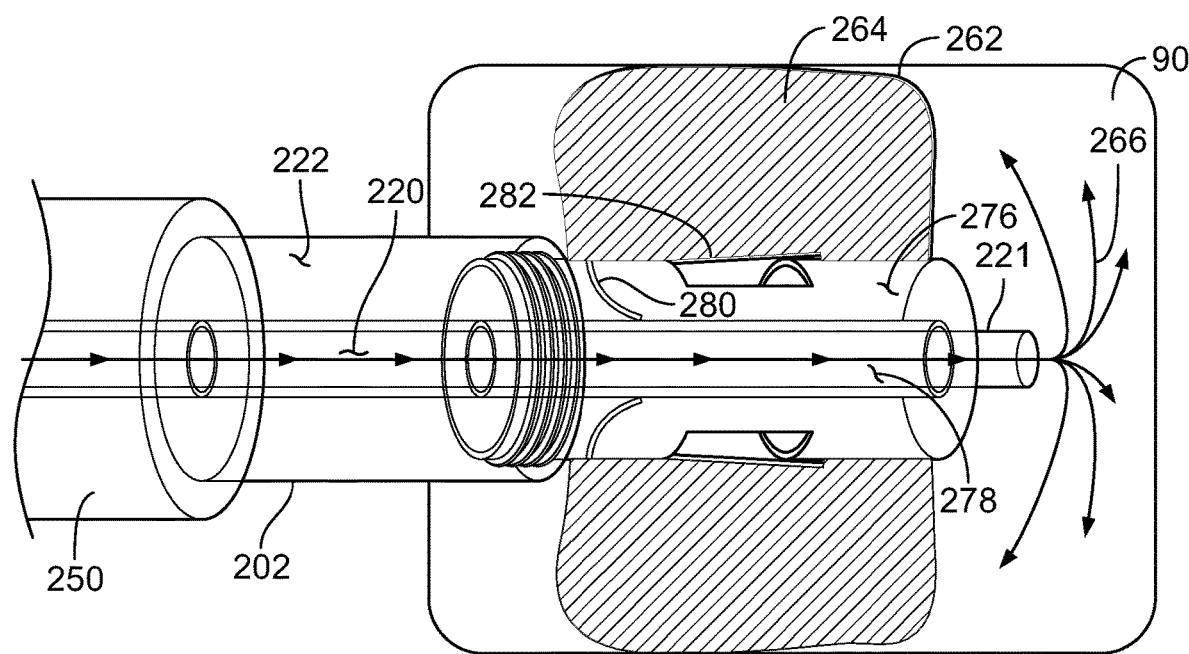
FIG. 6 illustrates that a balloon device of the multi-functionality head is in an inflated status, and a bone filler is delivered into a vertebral body.
Figure 7:
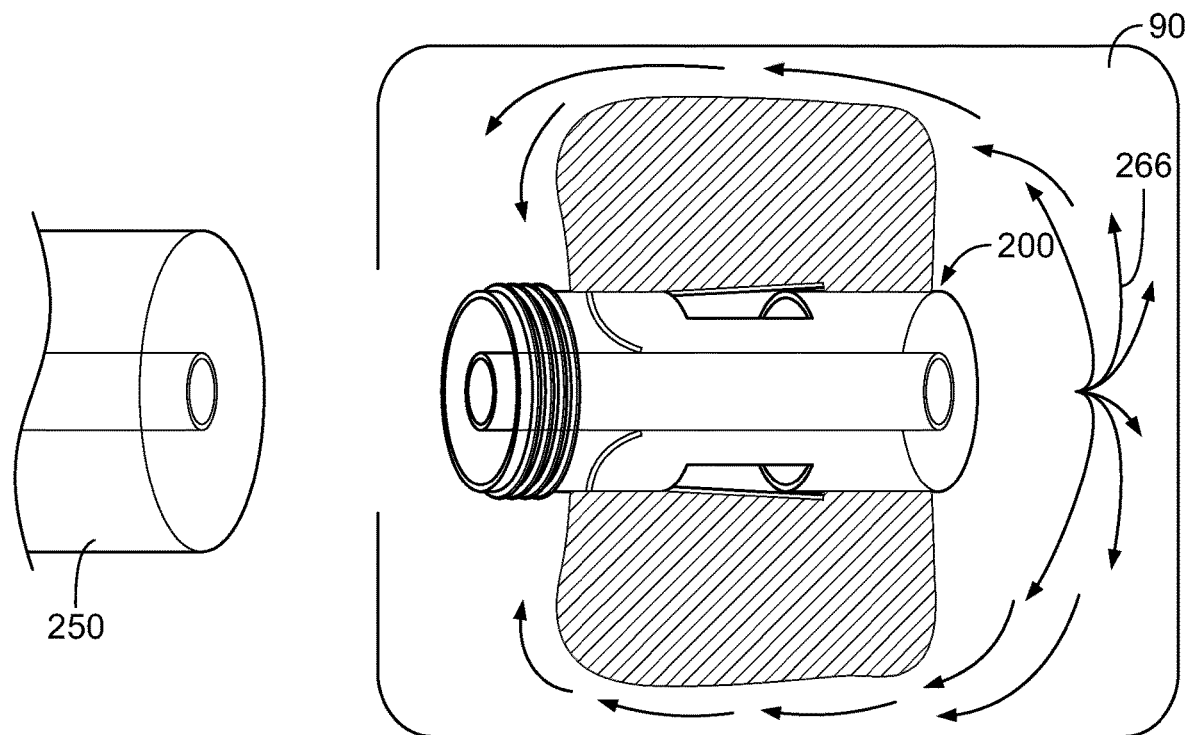
FIG. 7 illustrates that the bone filler fills in the vertebral body.

Referring to FIGS. 5-7, an example method includes inserting the multi-functionality head 200 into a compressed or fractured vertebral body 90. The multi-functionality head 200, which is coupled (e.g., screw threaded, or other suitable manners) to the distal end 210 of the shaft 202, is inserted with the shaft 202 through the bone introducer needle 250 that has been placed through the patient's body toward the vertebral body 90. As described herein, the bone filler channel 220 and the balloon fluid channel 222 of the shaft 202 are in fluid communication with the second conduit 278 and the first conduit 276 of the multi-functionality head 200, respectively, when the multi-functionality head 200 is attached to the shaft 202. As indicated with arrows in FIG. 5, the balloon fluid 264 can be delivered through the balloon fluid channel 222 of the shaft 202 and the first conduit 276 of the multi-functionality head 200. The flow of the balloon fluid can open the first valve 280 and the second valve 282 so that the balloon fluid can pass through the balloon ports 290 and fill in the balloon device 262, thereby inflating the balloon device 262. As such, when the multi-functionality head 200 is placed within the vertebral body 90, the balloon fluid can be injected into the balloon device 262 through the balloon fluid channel 222 of the shaft 202 and the first conduit 276 of the multi-functionality head 200 until the balloon device 262 is inflated to secure a desired height in the vertebral body 90.

Referring to FIG. 6, the balloon device 262 of the multi-functionality head 200 is in an inflated status within the vertebral body 90, and a bone filler 266 is now delivered into the vertebral body 90. The bone filler can be delivered through the bone filler channel 220 of the shaft 202 and the second conduit 278 of the multi-functionality head 200 and into the vertebral body 90. For example, once the balloon device 262 has been inflated to have a desired height within the vertebral body 90, the bone filler can be injected into, and fill in, the vertebral body 90 through the bone filler channel 220 of the shaft 202 and the second conduit 278 of the multi-functionality head 200, as indicated as arrows in FIG. 6. In some implementations, a filler needle 221 is introduced through the bone filler channel 220 of the shaft 20 and the second conduit 278 of the multi-functionality head 200, and the bone filler can be injected through the filler needle 221.

Referring to FIG. 7, the bone filler 266 fills in the vertebral body 90 to restore the vertebral body 90. As illustrated, once the height of the vertebral body 90 is restored, the shaft 202 can be decoupled from the multi-functionality head 200 and removed through the bone introducer needle 250. For example, the shaft 202 can be removed from the multi-functionality head 200 by unscrewing the distal end 210 of the shaft 202 from the threaded portion 277 of body 260 of the multi-functionality head 200. After the shaft 202 is removed, the multi-functionality head 200 can remain within the restored vertebral body 90 with the balloon device 262 being inflated.

FIG. 7A illustrates another example kyphoplasty apparatus including an example multi-functionality head 200A and an example elongate shaft 202A. The multi-functionality head 200A is configured similarly to the multi-functionality head 200 with modifications. For example, similarly to the first valve 280, the multi-functionality head 200A includes a first valve 280A, which can be a one-way conical valve made of a flexible material (e.g., rubber). As illustrated in FIG. 5, the first valve 280 of the multi-functionality head 200 is illustrated as being fixed at an outer diameter (i.e., an interior thereof) of the first conduit 276 and being openable around the second conduit 278. However, the first valve 280A of the multi-functionality head 200 can be configured to be fixed around the second conduit 278 (at an edge of the first valve 280A close to the proximate body end 274) and openable around the outer diameter (i.e., an interior thereof) of the first conduit 276 (at an opposite edge of the first valve 280A close to the distal body end 272).

The multi-functionality head 200A includes a second valve 282A having the same or similar functionality as the second valve 282 of the multi-functionality head 200. However, the second valve 282A can be configured in the form of a sleeve (e.g., a one-way sleeve valve) made of flexible material (e.g., rubber). Similarly to the second valve 282, the second valve 282A in the form of a one-way sleeve valve can be fixed at an edge close to the proximate body end 274 and openable at an opposite end close to the distal body end 272.

The multi-functionality head 200A can include one or more spring-biased footplates 279. The footplates 279 can be arranged and configured such that their free ends are pressed against the inner surface of the bone introducer needle 250, thereby being collapsed inside the bone introducer needle 250, when the bone introducer needle 250 surrounds a portion of the multi-functionality head 200A in which the footplates 279 are located. Then, when the bone introducer needle 250 is pulled back, the multi-functionality head 200A becomes unsheathed, and the footplates 279 return to their original shape (open or expanded position) by the spring force.

In addition or alternatively to the threaded portion 277, the multi-functionality head 200A can provide a non-threaded structure that can detachably couple the head 200A to a shaft 202A. For example, the multi-functionality head 200A is configured for a snap-fit (e.g., snap on/off) with the shaft 202A. The multi-functionality head 200A can include water-tight seals 275 at the proximate body end 274 of the head 200A, such as at the ends of the first and second conduits 276 and 278 at the proximate body end 274 of the head 200A. The multi-functionality head 200A can be sealingly snap-fitted to the shaft 202A with the first and second conduits 276 and 278 being aligned with the balloon fluid channel 222 and the bone filler channel 220 of the shaft 202A. Further, the multi-functionality head 200A can be simply removed from the shaft 202A by, for example, axially pulling the shaft 202A away from the multi-functionality head 200A.

The multi-functionality head 200, 200A can have one, some or all of the threaded portion 277, the spring-biased footplates 279, and the snap-fit structure with the water-tight seals 275.

In operation, the multi-functionality head 200A is snap-fitted to the shaft 202A, and the assembly of the head 200A and the shaft 202A is inserted into the bone introducer needle 250 such that the footplates 279 are collapsed inside the bone introducer needle 250. Then, the bone introducer needle 250 and the assembly of the head 200A and the shaft 202A are pushed toward a vertebral body until the head 200A is positioned in a desired location within the vertebral body. Then, the bone introducer needle 250 can be pulled back until the footplates 279 of the head 200A are released from the interior of the needle 250. The multi-functionality head 200A is then positioned at least partially unsheathed inside the vertebral body. After the balloon device 262 is inflated and the cavity in the vertebral body is filled with a body cement, the shaft 202A is pulled back, and in some instances the head 200A snap-fitted to the shaft 202A might be moved together with the shaft 202A. However, the movement of the head 200A may be limited by the footplates 279 when the footplates 279 become abutted with the distal end of the bone introducer needle 250 or other structures of the vertebral body. A further pull-back of the shaft 202A may permit the head 200A to be detached from the shaft 202A so that the head 200A remains within the vertebral body.

Figure 8:
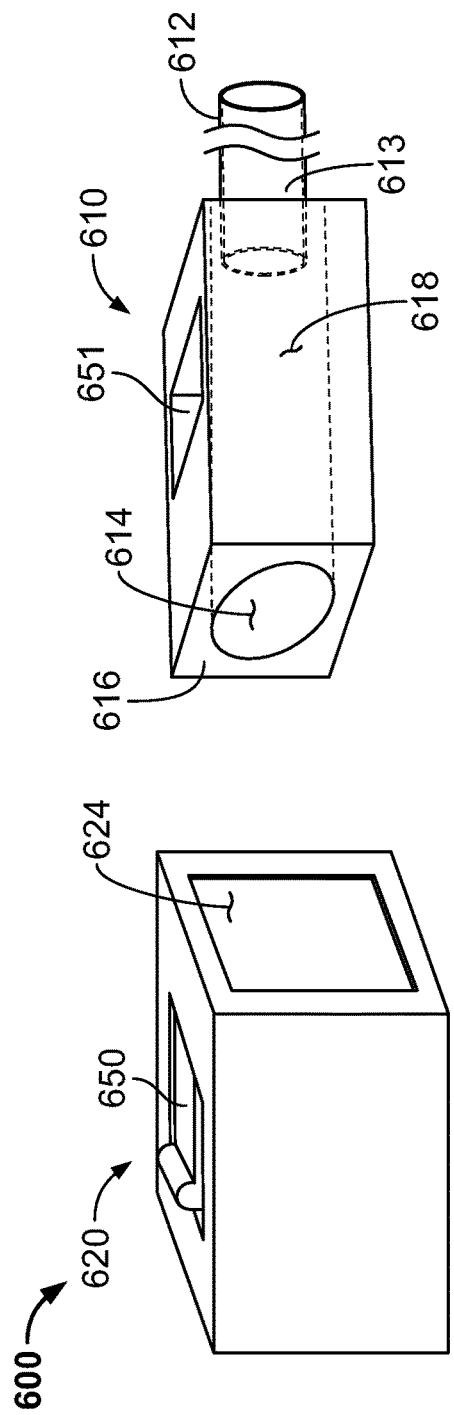
FIG. 8 illustrates an example connection system in the kyphoplasty system.

Referring now to FIG. 8, some embodiments of the kyphoplasty system 100 can include a connection system 600. Preferably, the connection system 600 is configured to provide compact, easy, and reliable engagement between instruments in the kyphoplasty system or other interventional procedures. Although the connection system 600 is primarily described in the kyphoplasty system 100, it is understood that the connection system 600 may be used in other interventional procedures.

The connection system 600 can include a first connector 610 and a second connector 620. The first connector 610 and the second connector 620 can be mounted to a first component 612 and a second component, respectively, and configured to operatively couple the first component 612 and the second component. As described herein, the first component 612 may include a bone introducer needle, a biopsy needle, other types of needles, cannulas, drill tips, a kyphoplasty apparatus (e.g., the shaft 202 mounting the multi-functionality device 200), and other suitable instruments for kyphoplasty. The second connector 620 can be coupled to a tool for controlling the second component. Such a tool can include a manual handle grip, a manual or electrical drill, and other suitable manual or electrical tools. For example, the second connector 620 is fixed to a tool, or integrally formed with a tool. Alternatively, the second connector 620 can be removably engaged with a tool. For example, a tool, such as a drill, has a socket configured to non-rotatably engage with the second connector 620. In some embodiments, the second connector 620 can be directly inserted into a socket of a tool. Alternatively, when the shape of the second connector 620 is not compatible (e.g., not complementary) with a socket of a tool (e.g., when the exterior shape of the second connector 620 has a rectangular cross section while the socket has a hexagonal cross sectional shape), an adapter (e.g., an adapter having a rectangular cross sectional interior to receive the second connector, and having a hexagonal cross sectional exterior to engage with the socket) can be used to be disposed between the second connector 620 and the socket of the tool.

As described herein, for example, the second connector 620 that may be part of a tool, such as a manual handle or an electronic drill, can be releasably engaged with (e.g., secured onto) the first connector 620 that mounts an instrument, such as a bone introducer needle, a biopsy needle, a drill, a kyphoplasty apparatus, etc., so that user's operation or manipulation of the tool is translated to the instrument mounted to the first connector 620.

The first connector 610 can be configured to at least partially insert within the second connector 620 and releasably couple with the second connector 620. For example, the second connector 620 has a cavity 624 configured to correspond to at least a portion of an exterior shape of the first connector 610 so that the first connector 610 is at least partially received within the cavity 624 of the second connector 610. In some implementations, the first connector 610 can include a connector port 614 that is open at a mating side 616 of the first connector 610 and provides an instrument passage 618 into a lumen 613 of the first component 612 attached at the other side of the mating end 616. This configuration can be used when the first component 612 mounted to the first connector 610 is a bone introducer needle or other types of needles or lumens for receiving another instrument. In other implementations, the first connector 610 can have a closed end at the mating side 616 (without a connector port 614).

In this depicted example, the first connector 610 and the second connector 620 can be referred to as an inner connector and an outer connector, respectively. The first and second connectors 610 and 620 are sized to have small form factors with respect to the first and second components, thereby providing sufficient spacing between different sets of instruments (e.g., the coupled first and second components) which are introduced into the patient and/or arranged in place.

The first connector 610 and the second connector 620 can be configured to be at least partially complimentary to prevent radial and/or axial movements of the first component 612 (and the first connector 610) relative to the second connector 620 when they are coupled. The first connector 610 can be configured to at least partially fit into the cavity 624 of the second connector 620 so that the first connector 610 does not substantially rotate within the second connector 620. For example, the exterior of the first connector 610 is shaped to be a cube, rectangular prism, or other polygonal prisms, and the cavity 624 of the second connector 620 can have an interior shape corresponding to the exterior of the first connector 610 so that the first connector 610 does not rotate about the second connector 610 when inserted into the cavity 624 of the second connector 610.

The connection system 600 can include an axial lock to prevent an axial movement of the first connector 610 relative to the second connector 620 when engaged with the second connector 620. For example, the second connector 620 includes a spring clasp 650 configured to releasably engage with a notch 651 of the first connector 610. An example of the axial lock is further described with reference to FIGS. 9A-9C and 10A-10J.

Figure 9A:
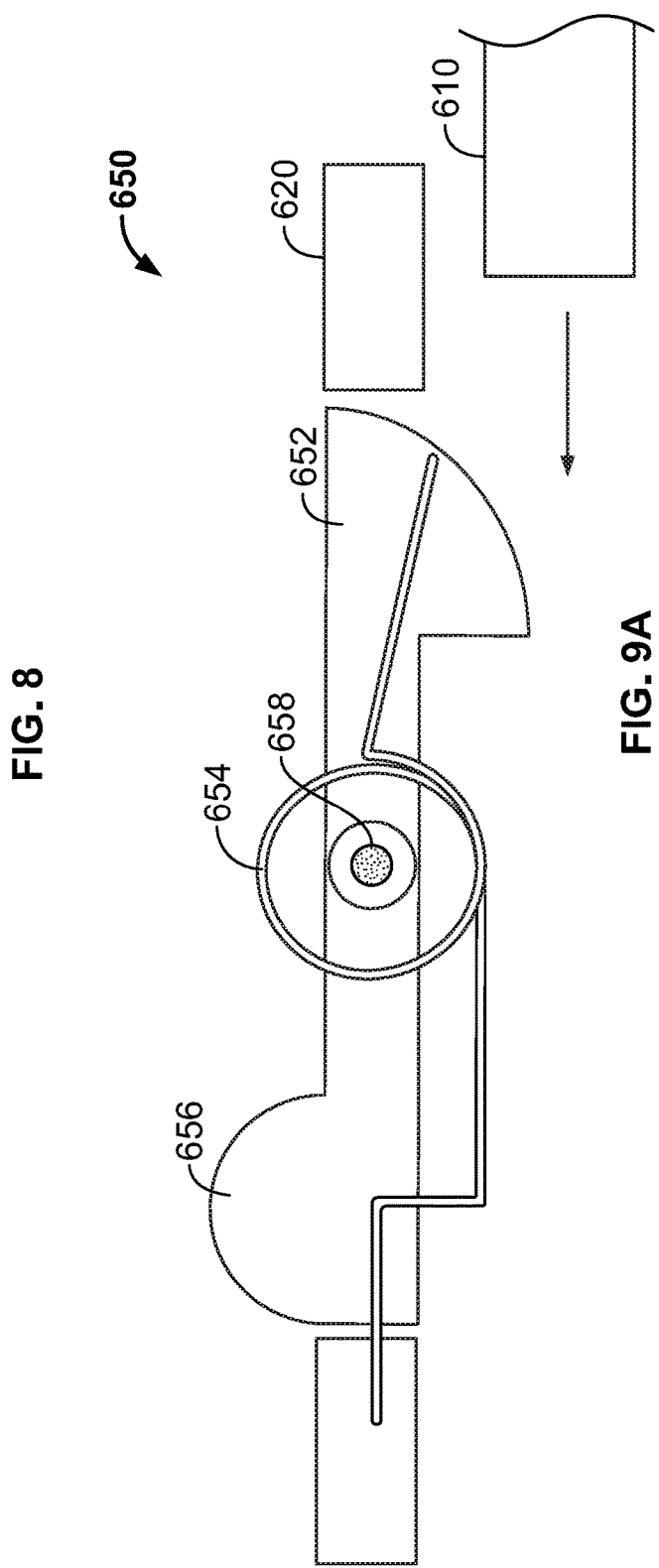
FIG. 9A is a side cross sectional view of an example spring clasp in a first position.

Referring to FIGS. 9A-9C, an example of the axial lock can include the spring clasp 650. FIG. 9A is a side cross sectional view of an example spring clasp of the first connector in a first (initial, released) position prior to engaging with the second connector. FIG. 9B is a side cross sectional view of the spring clasp in a second (transitional) position as the second connector is inserted into the first connector. FIG. 9C is a side cross sectional view of the spring clasp in a third (final, engaged) position after the second connector is inserted into the first connector.

The spring clasp 650 can be disposed in the second connector 620 and is configured to allow the second connector 620 to connect with the first connector 610 by simply inserting the first connector 610 to the second connector 620. For example, the spring clasp 650 is pivotally arranged in the second connector 620 and includes a hook portion 652. As illustrated in FIG. 9A, the spring clasp 650 of the second connector 620 is biased to a hooked position before the first connector 610 is inserted into the second connector 620. For example, the spring clasp 650 includes a spring element 654 arranged to maintain the spring clasp 650 to be generally flush with a portion (e.g., a top surface) of the second connector 620 and bias the hook portion 652 toward the inside of the second connector 610 (e.g., toward the first connector 610 being inserted into the second connector 610).

As illustrated in FIG. 9B, as the first connector 610 is inserted into the second connector 620, the first connector 610 engages with the spring clasp 650 of the second connector 620 and pivots the spring clasp 650 against the biasing force of the spring clasp 650. For example, as the first connector 610 is inserted, the spring clasp 650 is in a transition position in which the hook portion 652 becomes to contact with a surface of the first connector 610 and is raised against the biasing force of the spring element 654. As illustrated in FIG. 9C, as the first connector 610 is further inserted into the second connector 620, the spring clasp 650 returns to the hooked position where the biasing force of the spring element 654 causes the hook portion 652 of the spring clasp 650 to snap in the notch 651 defined on the first connector 610.

In addition or alternatively, the spring clasp 650 includes a release portion 656 that can be pushed to release the hook portion 652 of the spring clasp 650 from the notch 651 of the first connector 620 so that the first connector 610 can be removed from the second connector 620. The release portion 656 is arranged opposite to the hook portion 652 with a pivot axis 658 of the spring clasp 650 arranged between the hook portion 652 and the release portion 656.

Figure 10A:
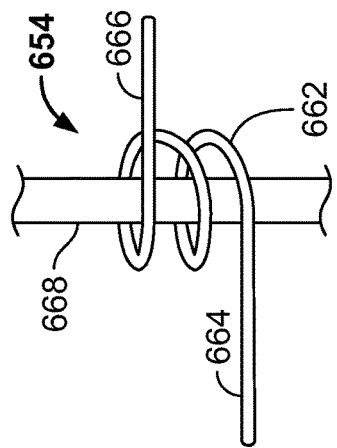
FIG. 10A is a side schematic view of an example spring element.
Figure 10B:
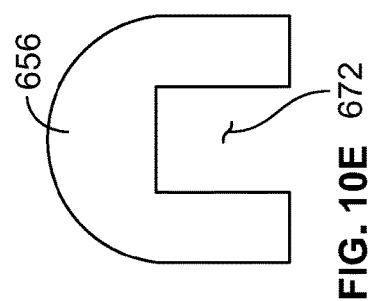
FIG. 10B illustrates an example arrangement of the spring element in the spring clasp 650.

Referring to FIGS. 10A-10J, an example of the spring clasp 650 is further described. In particular, FIG. 10A is a side schematic view of an example of the spring element 654, and FIG. 10B illustrates an example arrangement of the spring element 654 in the spring clasp 650. As illustrated, the spring element 654 can be a coil spring having a winding part 662 with a first leg 664 and a second leg 666. The winding part 662 can be arranged around a pivot pin 668. The first leg 664 can abut with a portion of the second connector 620, while the second leg 666 can abut with a portion of the body 660 of spring clasp 650.

Figure 10C:
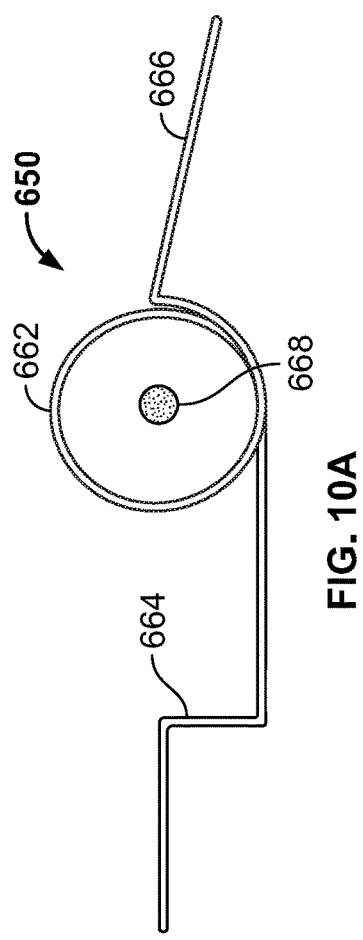
FIG. 10C is a side view of an example body of the spring clasp.
Figure 10D:
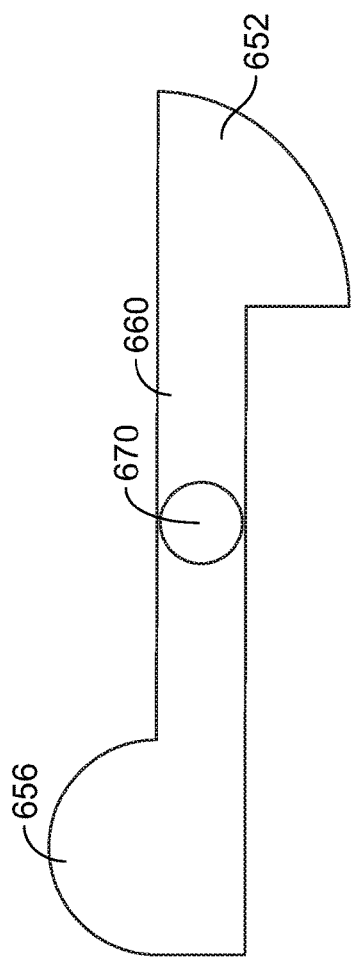
FIG. 10D is a top view of the body of the spring clasp.
Figure 10E:
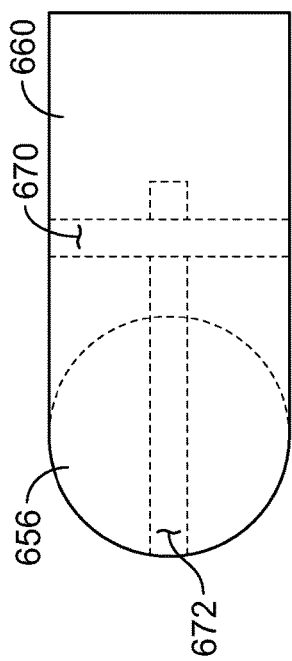
FIG. 10E is a front view of the body of the spring clasp.

FIG. 10C is a side view of an example body 660 of the spring clasp 650, FIG. 10D is a top view of the body 660 of the spring clasp 650, and FIG. 10E is a front view of the body 660 of the spring clasp 650. The body 660 includes a pin hole 670 configured to receive the pivot pin 668 that can be fixed to a body of the second connector 620 so that the body 660 of the spring clasp 650 rotates around the pivot pin 668. The body 660 can include the hook portion 652 and the release portion 656 with the pin hole 670 arranged therebetween. The body 660 provides a spring recess 672 configured to at least partially receive and the spring element 654 in place.

Figure 10F:
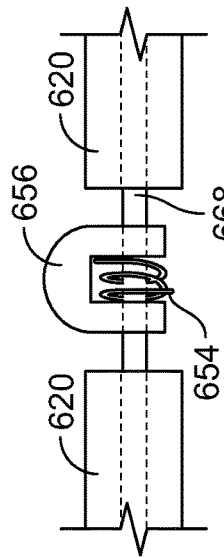
FIG. 10F is a schematic front view of the spring clasp in a hook position.
Figure 10G:
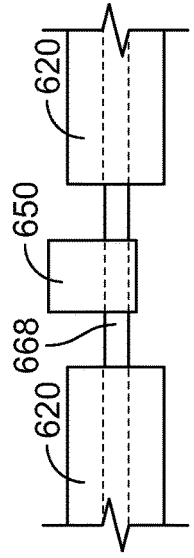
FIG. 10G is a schematic rear view of the spring clasp in the hook position.
Figure 10H:
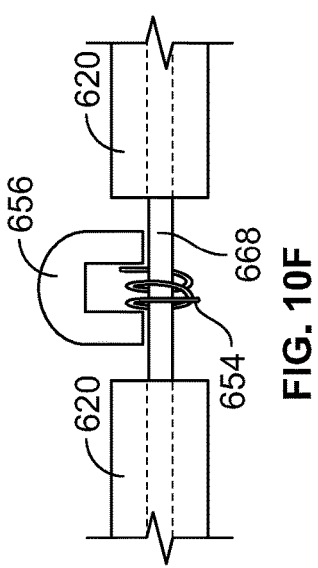
FIG. 10H is a schematic front view of the spring clasp in a transition position.
Figure 10I:
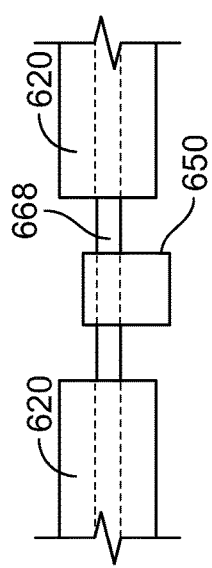
FIG. 10I is a schematic rear view of the spring clasp in the transition position.
Figure 10J:
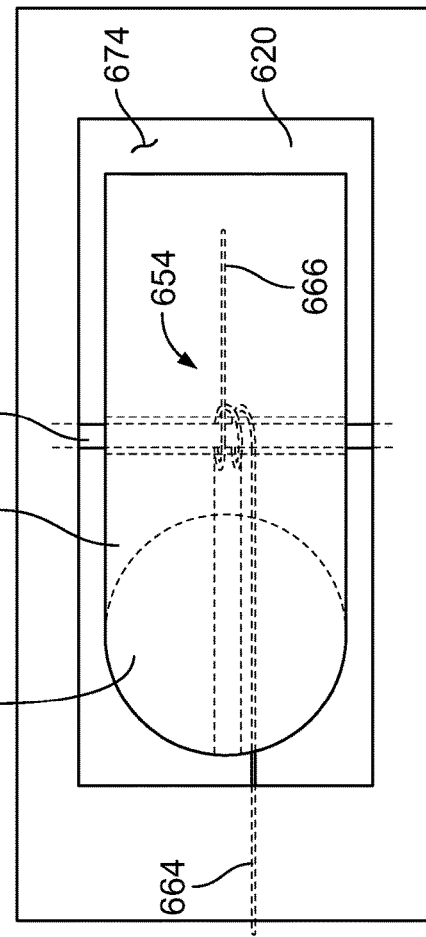
FIG. 10J is a schematic top view of the spring clasp coupled to a connector.

Referring to FIG. 10J, which is a schematic top view of the spring clasp 650 coupled to the second connector 620, the second connector 620 includes an aperture 674 configured to receive the spring clasp 650. The pivot pin 668 is attached to the body of the second connector 620 across the aperture 674. The spring element 654 can be disposed around the pivot pin 668 with the first leg 664 extending and abutting with the body of the second connector 620, and the second leg 666 abutting with the body 660 adjacent the hook portion 652. The spring element 654 is configured to generate a force that biases the hook portion 652 downwards (e.g., towards the notch 651 of the first connector 610).

FIG. 10F is a schematic front view of the spring clasp 650 in a hook position, and FIG. 10G is a schematic rear view of the spring clasp 650 in the hook position. When the first connector 610 is properly engaged with the second connector 620, or when the first connector 610 is not inserted into the second connector 620, the hook portion 652 is lowered to a level sufficient to snap in the notch 651 of the first connector 610 while the release portion 656 of the spring clasp 650 is raised relative to a position of the release portion 656 in a transition position in FIGS. 10H and 10I.

FIG. 10H is a schematic front view of the spring clasp 650 in a transition position, and FIG. 10I is a schematic rear view of the spring clasp 650 in the transition position. As the first connector 610 is received into the second connector 620, the hook portion 652 is raised against the biasing force of the spring element 654, and the release portion 656 is lowered relative to the position of the release portion 656 in the hook position in FIGS. 10F and 10G.

Figure 11A:
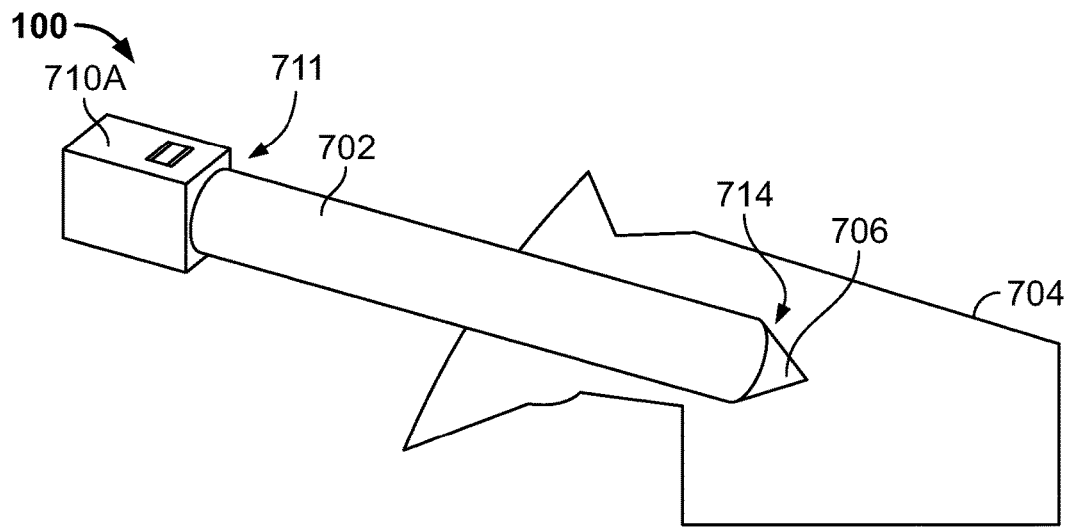
FIG. 11A illustrates an example kyphoplasty procedure in which a bone introducer needle is inserted into a compressed vertebral body.

FIGS. 11A-11I illustrate an example kyphoplasty procedure using the kyphoplasty system 100. Referring to FIG. 11A, a bone introducer needle 702 is inserted into a compressed vertebral body 704 (e.g., the vertebral body 90). The bone introducer needle 702 can be used for the bone introducer needle 250 described herein. The bone introducer needle 702 can have various sizes. In some implementations, the bone introducer needle 702 can range from 5 gauge to 20 gauge. In other implementations, the bone introducer needle 702 is sized about 10 gauge.

The bone introducer needle 702 can be introduced with an inner stylette 706. The stylette 706 can be inserted into the bone introducer needle 702 to stiffen the bone introducer needle 702 and maintain its form while the bone introducer needle 702 is inserted into the vertebral body 704. The stylette 706 can extend out from a distal end 714 of the bone introducer needle 702.

The bone introducer needle 702 can be mounted to a first connector 710A at a proximate end 711 of the bone introducer needle 702. The first connector 710A can be configured identically or similarly to the first connector 610, and the bone introducer needle 702 is an example of the first component 612, as described in FIG. 8. In some implementations, the first connector 710A of the bone introducer needle 702 is coupled to a second connector (similar to the second connector 620 in FIG. 8) which is part of a tool, such as a manual handle or a drill, so that the bone introducer needle 702 is introduced into a vertebral body by gripping and manipulating the tool.

Figure 11B:
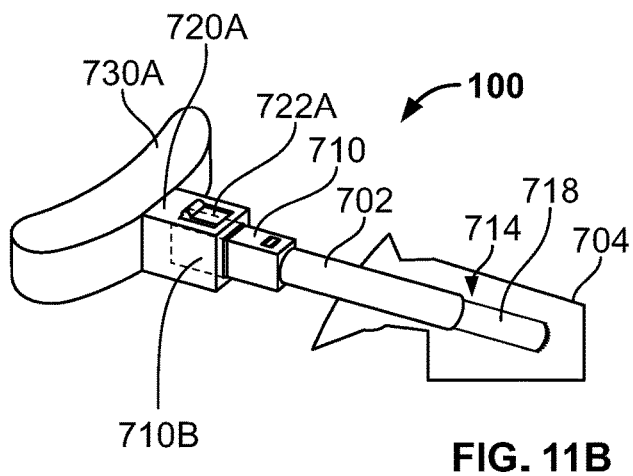
FIG. 11B illustrates an example kyphoplasty procedure in which a bone biopsy needle is introduced into the vertebral body.
Figure 11C:
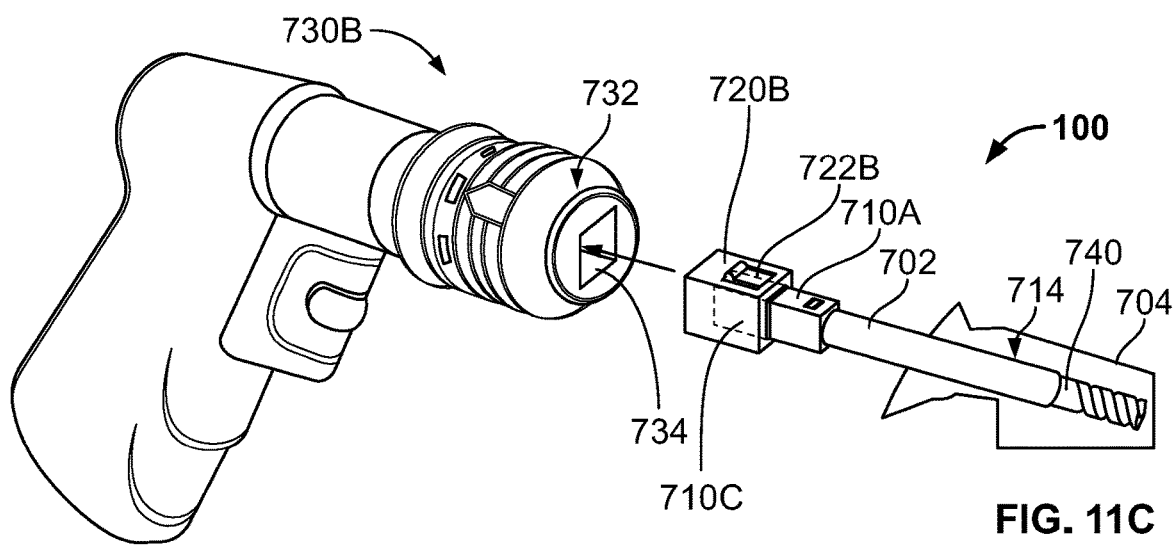
FIG. 11C illustrates an example kyphoplasty procedure in which a bone drill bit is introduced into the vertebral body.

Referring to FIG. 11B, a biopsy needle 718, which can be for bone biopsy or soft tissue biopsy, is coaxially introduced into the vertebral body 704 through the bone introducer needle 702. The biopsy needle 718 is used to remove bone samples from the vertebral body. Such bone samples can be examined to find out if cancer or other abnormal cells are present. The biopsy needle 718 can be mounted to a first connector 710B at a proximate end. As such, the biopsy needle 718 is an example of a first component 612, as described in FIG. 8. The first connector 710B can be engaged with and secured in a second connector 720A. The second connector 720A can be part of, or connected to, a tool such as a manual handle 730A (FIG. 11B) or an electronic drive tool 730B (FIG. 11C). In the illustrated example, the second connector 720A can be part of a tool 730A (e.g., a manual handle). The second connector 720A can be configured identically or similarly to the second connector 620, as described in FIG. 8. In some implementations, the bone biopsy needle 712 can range from 7 gauge to 20 gauge. In other implementations, the bone biopsy needle 712 is sized about 12 gauge. The biopsy needle 718 mounted to the first connector 710B can be arranged and advanced coaxially with the bone introducer needle 702 such that the first connector 710B of the biopsy needle 718 can be disposed behind the first connector 710A of the bone introducer needle 702. Because the first connector 710B of the biopsy needle 718 is secured to the second connector 720A of the tool 730A, the biopsy needle 718 can be controlled by manipulating the tool 730A.

The second connector 720A can be releasably coupled to the first connector 710B, as described with reference to FIG. 8. The first connector 710B can be at least partially inserted into a cavity (e.g., the cavity 624) of the second connector 720A and releasably coupled with the second connector 720A using a lock mechanism 722A, such as the spring clasp 650. When the first connector 710B is coupled with the second connector 720A, the bone biopsy needle 712 passes through the bone introducer needle 702 with a distal end of the bone biopsy needle 712 extending out from the distal end 714 of the bone introducer needle 702.

Referring to FIG. 11C, a bone drill bit 740 is coaxially introduced into the vertebral body 704 through the bone introducer needle 702. The bone drill bit 740 is used to create a cavity in the vertebral body. The bone drill bit 740 can be mounted to a first connector 710C at a proximate end. As such, the bone drill bit 740 is an example of a first component 612, as described in FIG. 8. The first connector 710C can be engaged with and secured in a second connector 720B which can be part of, or connected to a tool such as the manual handle 730A (FIG. 11B) or the electronic drive tool 730B (FIG. 11C). In the illustrated example, the second connector 720B is connected to the electronic drive tool 730B. The second connector 720B can be configured as the second connector 620, as described in FIG. 8. In some implementations, the bone drill bit 740 can range from 7 gauge to 20 gauge. In other implementations, the bone drill bit 740 is sized about 12 gauge. The bone drill bit 740 mounted to the first connector 710C can be arranged and advanced coaxially with the bone introducer needle 702 such that the first connector 710C of the bone drill bit 740 can be disposed behind the first connector 710A of the bone introducer needle 702. Because the first connector 710C of the bone drill bit 740 is secured to the second connector 720B of the tool 730B, the bone drill bit 740 can be operated by controlling the tool 730B.

The second connector 720B of the bone drill bit 740 can be releasably coupled to the first connector 710C, as described with reference to FIG. 8. The first connector 710C can be at least partially inserted into a cavity (e.g., the cavity 624) of the second connector 720B and releasably coupled with the second connector 720B using a lock mechanism 722B, such as the spring clasp 650. When the first connector 710C is coupled with the second connector 720B, the bone drill bit 740 passes through the bone introducer needle 702 with a distal end of the bone drill bit 740 extending out from the distal end 714 of the bone introducer needle 702.

The tool 730B can fix or mount the second connector 720A so that the bone drill bit 740 can be operated by the tool 730B handled by a user. For example, the tool 730B can be a powered or manual handheld tool (e.g., a drill) configured to attach a variety of instruments and spin them about their axis. The tool 730B can include a coupling feature 732 configured to detachably mount the second connector 720B. Examples of the coupling feature 732 include a socket 734 to fit the second connector 720B. The socket 734 can be configured to be complementary to an exterior shape of the second connector 720B, so that the second connector 720B can be prevented from rotating relative to the drill when the second connector 720B is received within the socket of the drill. In addition or alternatively, the coupling feature 732 can include a chuck operable to hold the second connector 720B. In some implementations, an adapter can be provided to be disposed between the second connector 720B and the socket 734, for example when the exterior shape of the second connector 720B is not complementary to the interior shape of the socket 734. In addition or alternatively, other types of fasteners, such as screws, clips, clamps, adhesives, magnets, etc., can be used to mount the second connector 720A to the drill.

Figure 11D:
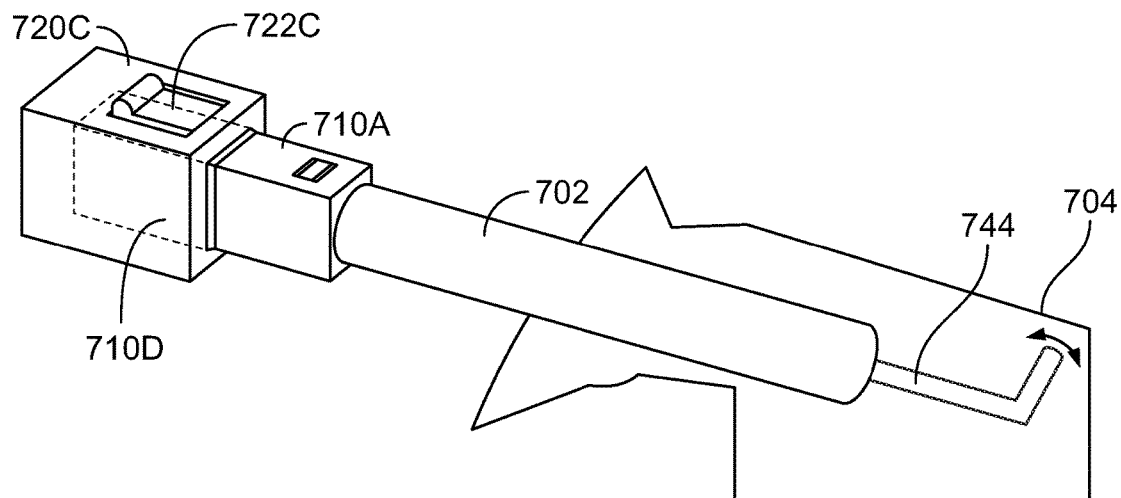
FIG. 11D illustrates an example kyphoplasty procedure in which a cavity curette is introduced into the vertebral body.

Referring to FIG. 11D, a cavity curette 744 is introduced into the vertebral body 704 through the bone introducer needle 702. The cavity curette 744 is used to remove (e.g., scrape and/or debride) debris in a cavity (e.g., the cavity created by a bone drill) created in the vertebral body. The cavity curette 744 can be mounted to a first connector 710D at a proximate end. As such, the cavity curette 744 is an example of a first component 612, as described in FIG. 8. The first connector 710D can be engaged with and secured in a second connector 720C which can be part of a tool, such as the tool 730A or 730B. The second connector 720C can be configured as the second connector 620, as described in FIG. 8. In some implementations, the cavity curette 744 can range from 7 gauge to 20 gauge. In other implementations, the cavity curette 744 is sized about 12 gauge. The cavity curette 744 mounted to the first connector 710D can be arranged and advanced coaxially with the bone introducer needle 702 such that such that the first connector 710D of the cavity curette 744 can be disposed behind the first connector 710A of the bone introducer needle 702. Because the first connector 710D of the cavity curette 744 is secured to the second connector 720C of a tool (e.g., the tool 730A or 730B), the cavity curette 744 can be operated by controlling the tool 730.

The second connector 720C of the cavity curette 744 releasably coupled to the first connector 710D, as described with reference to FIG. 8. The first connector 710D can be at least partially inserted into a cavity (e.g., the cavity 624) of the second connector 720C and releasably coupled with the second connector 720C using a lock mechanism 722C, such as the spring clasp 650. When the first connector 710D is coupled with the second connector 720C, the cavity curette 744 passes through the bone introducer needle 702 with a distal end of the cavity curette 744 extending out from the distal end 714 of the bone introducer needle 702.

Figure 11E:
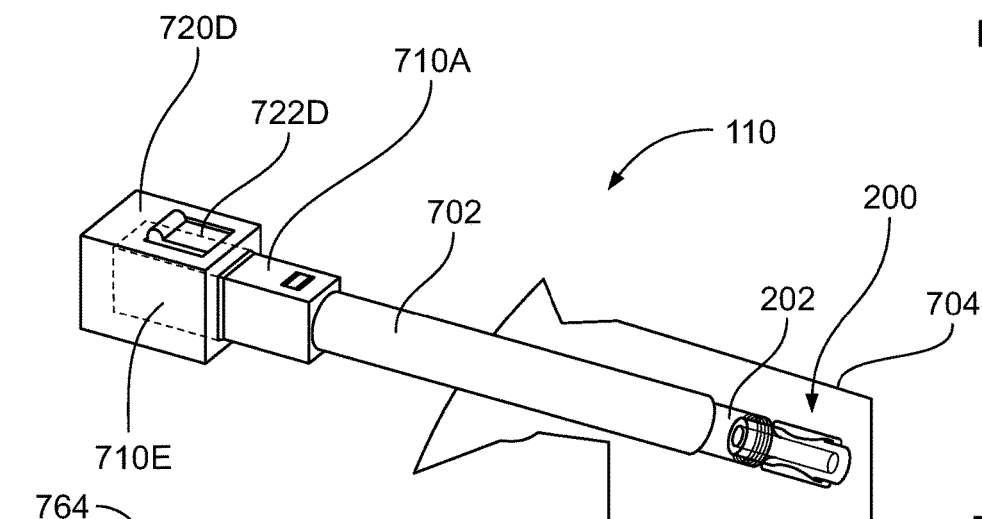
FIG. 11E illustrates an example kyphoplasty procedure in which a kyphoplasty apparatus is introduced into the vertebral body.

Referring to FIG. 11E, the kyphoplasty apparatus 110 is coaxially introduced into the vertebral body 704 through the bone introducer needle 702. As described herein, the kyphoplasty apparatus 110 can include the multi-functionality head 200 and the shaft 202 detachably coupled to the multi-functionality head 200. A proximate end (e.g., the proximate end 212) of the shaft 202 can be mounted to a first connector 710E. As such, the shaft 202 (with the multi-functionality head 200) is an example of the second component, as described in FIG. 8. The first connector 710E can be engaged with and secured in a second connector 720D which is part of a tool, such as the tool 730A or 730B. The second connector 720D can be configured as the second connector 620, as described in FIG. 8. In some implementations, the shaft 202 and/or the multi-functionality head 200 can range from 7 gauge to 20 gauge. In other implementations, the shaft 202 and/or the multi-functionality head 200 are sized about 12 gauge. The shaft 202 mounted to the first connector 710E can be arranged and advanced coaxially with the bone introducer needle 702 such that the first connector 710E of the shaft 202 can be disposed behind the first connector 710A of the bone introducer needle 702. Because the first connector 710E of the shaft 202 is secured to the second connector 720D of a tool, the shaft 202 with the multi-functionality head 200 can be inserted and manipulated by handling the tool.

The second connector 720D of the kyphoplasty apparatus 110 can be releasably coupled to the first connector 710E, as described with reference to FIG. 8. The first connector 710E can be at least partially inserted into a cavity (e.g., the cavity 624) of the second connector 720D and releasably coupled with the second connector 720D using a lock mechanism 722D, such as the spring clasp 650. When the first connector 710E is coupled with the second connector 720D, the kyphoplasty apparatus 110 passes through the bone introducer needle 702 with the multi-functionality head 200 and/or a distal end of the shaft 202 extending out from the distal end 714 of the bone introducer needle 702.

Figure 11F:
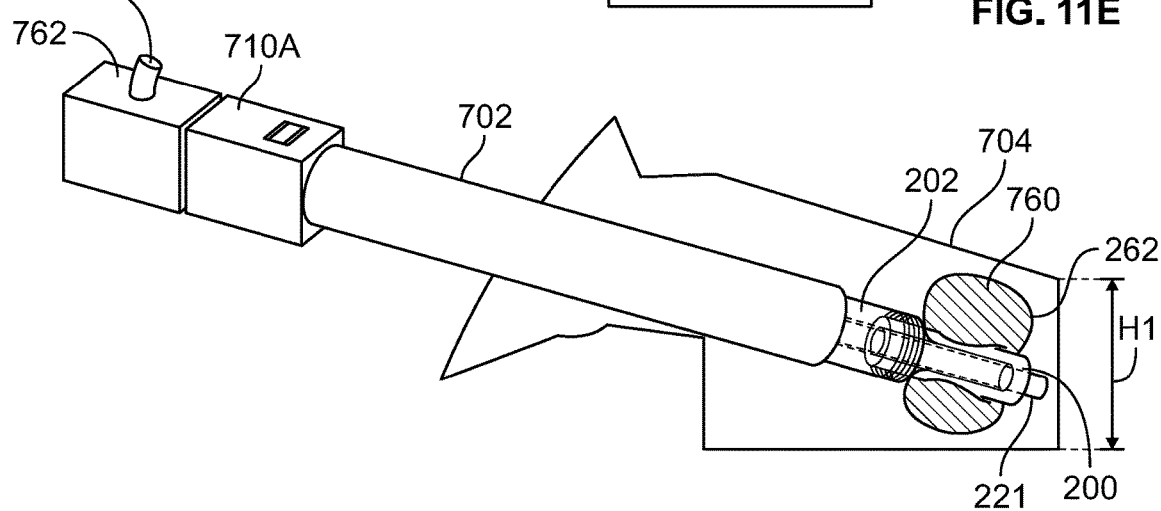
FIG. 11F illustrates an example kyphoplasty procedure in which a balloon inflation fluid is delivered to inflate a balloon device.
Figure 11G:
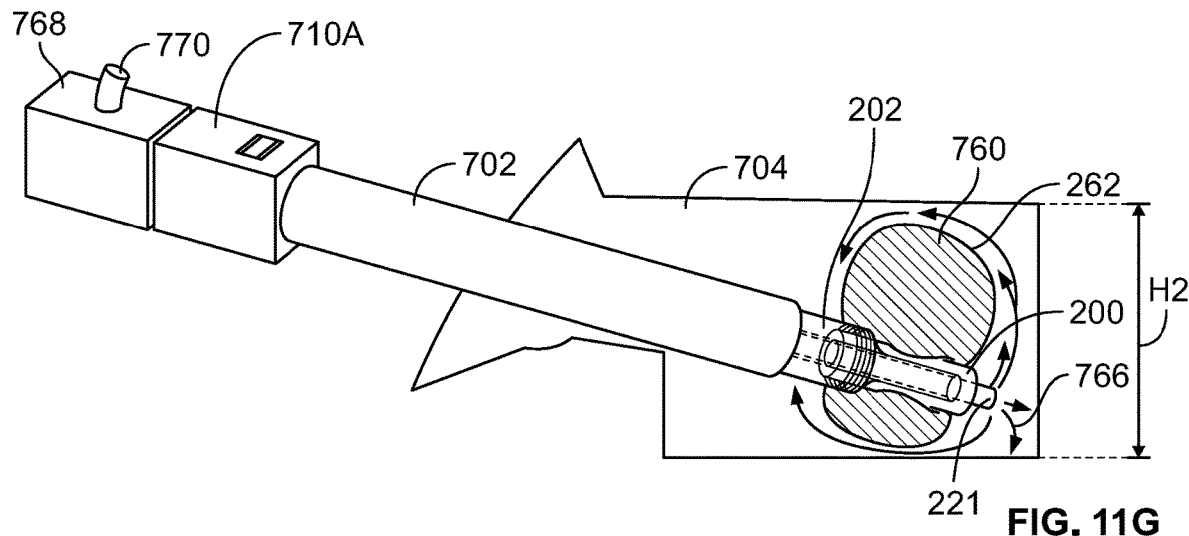
FIG. 11G illustrates an example kyphoplasty procedure in which a bone filler is delivered into the vertebral body.

Referring to FIG. 11F, a balloon inflation fluid 760 (e.g., the balloon fluid 264) is delivered through the shaft 202 and the multi-functionality head 200 into the balloon device 262 and fill in the balloon device 262, thereby inflating the balloon device 262. The inflated balloon device 262 can restore a height of the vertebral body 704 (e.g., from H1 as shown in FIG. 11F to H2 as shown in FIG. 11G). As also described in FIG. 5, the balloon inflation fluid 760 can be delivered through the balloon fluid channel 222 of the shaft 202 and the first conduit 276 of the multi-functionality head 200. In some implementations, the filler needle 221 is introduced through the bone filler channel 220 of the shaft 202 and the second conduit 278 of the multi-functionality head 200 so that a bone filler can be injected through the filler needle 221 (FIG. 11G). The shaft 202 can be connected to a balloon fluid source through a connector 762 having a port 764 being fluid communication with the balloon fluid source. The connector 762 can be disposed behind the first connector 710A of the bone introducer needle 702.

Referring to FIG. 11G, once the balloon device 262 is inflated with the balloon inflation fluid 760, a bone filler 766 (e.g., the bone filler 266) is delivered through the shaft 202 or the filler needle 221 introduced through the shaft 202, and then through the multi-functionality head 200 into the vertebral body 704. As also shown in FIG. 6, once the balloon device 262 has been inflated, the bone filler 765 can be injected into, and fill in, the vertebral body 704 through the bone filler channel 220 of the shaft 202 and the second conduit 278 of the multi-functionality head 200.

The shaft 202 can be connected to a bone filler source through a connector 768 having a port 770 being fluid communication with the balloon fluid source. In some implementations, the connector 768 can be the connector 762 in FIG. 11F which may be configured to permit for the balloon fluid and the bone filler to be delivered therethough selectively. For example, either or both of the connectors 762, 768 can be configured to selectively supply a balloon inflation fluid and a bone filler through the shaft 202 of the kyphoplasty apparatus 110. The connectors 762, 768 can be fluidly connected to the bone filler source 230 (and the actuator 232) and the balloon fluid source 240 (and the balloon controller 242) as described with reference to FIG. 2. The connectors 762, 768 can be configured as a single device that is in fluid communication with both the bone filler source 230 (and the actuator 232) and the balloon fluid source 240 (and the balloon controller 242). Alternatively, the connector 762 can be configured solely for delivery of a balloon inflation fluid and fluidly connected to the balloon fluid source 240 (and the balloon controller 242). The connector 768 can be configured solely for delivery of a bone filler and fluidly connected to the bone filler source 230 (and the actuator 232).

Figure 11H:
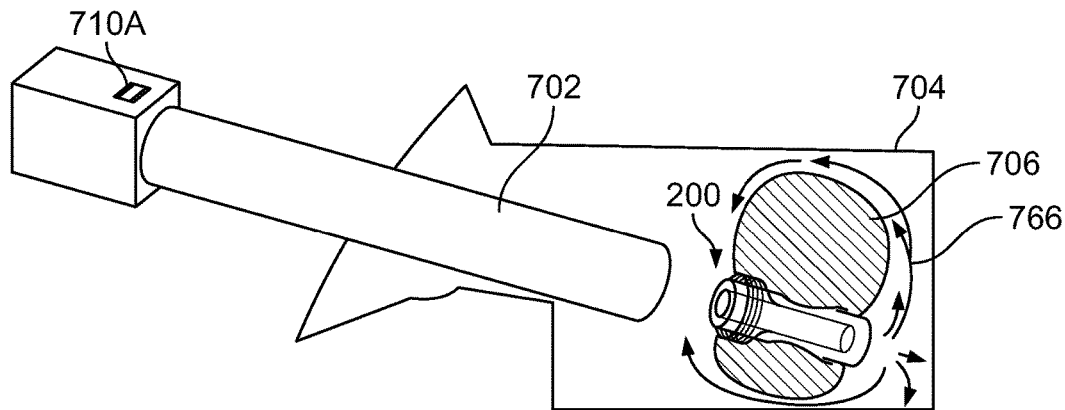
FIG. 11H illustrates an example kyphoplasty procedure in which a shaft is removed from the vertebral body.

Referring to FIG. 11H, once the bone filler 766 at least partially fill in the vertebral body 704, the shaft 202 is removed from the vertebral body 704. As also described in FIG. 7, the shaft 202 can be removed from the multi-functionality head 200 by unscrewing the distal end 210 of the shaft 202 from the threaded portion 277 of body 260 of the multi-functionality head 200.

Figure 11I:
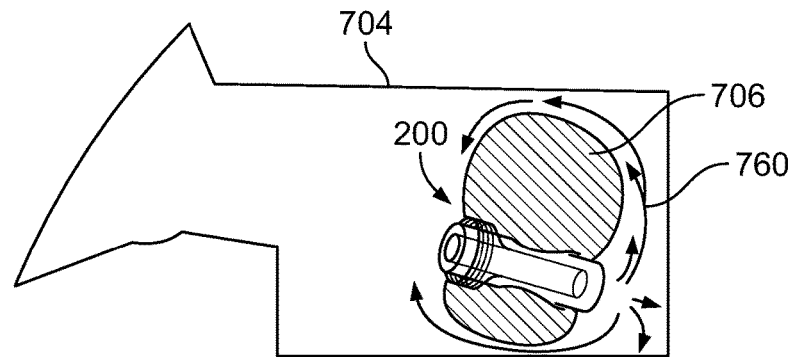
FIG. 11I illustrates an example kyphoplasty procedure in which the bone introducer needle is removed from the restored vertebral body.

Referring to FIG. 11I, the bone introducer needle 702 is removed from the restored vertebral body 704. The restored shape of the vertebral body 704 can be maintained by the inflated balloon device 262 of the multi-functionality head 200, as well as the bone filler that fills the vertebral body 704.

Figure 12A:
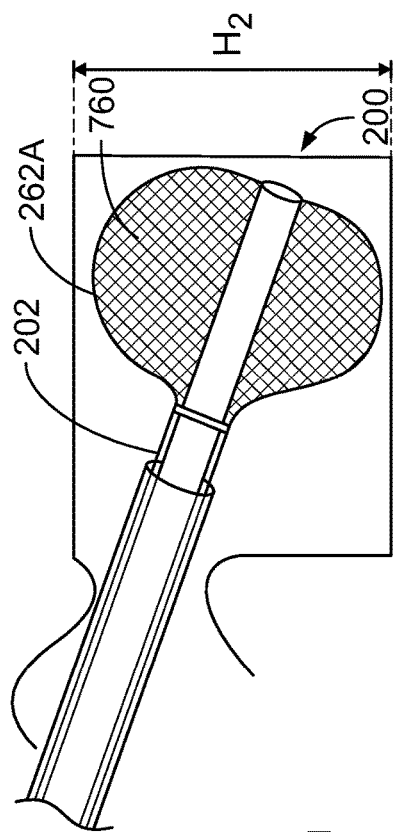
FIG. 12A illustrates an example kyphoplasty procedure that includes a single multi-functionality head with a spherical inflated balloon.
Figure 12B:
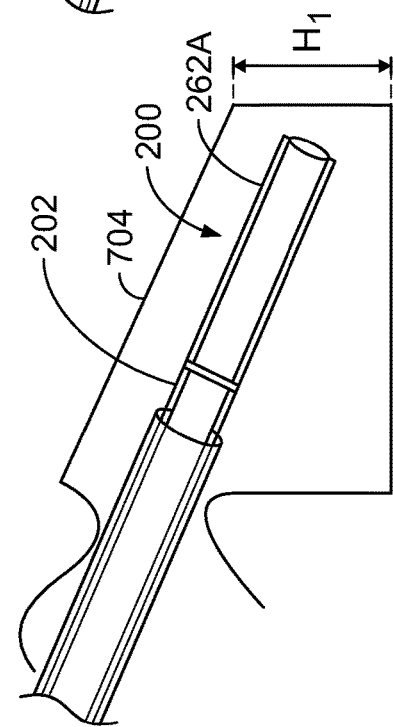
FIG. 12B illustrates an example kyphoplasty procedure with the multi-functionality head of FIG. 12A.
Figure 12C:
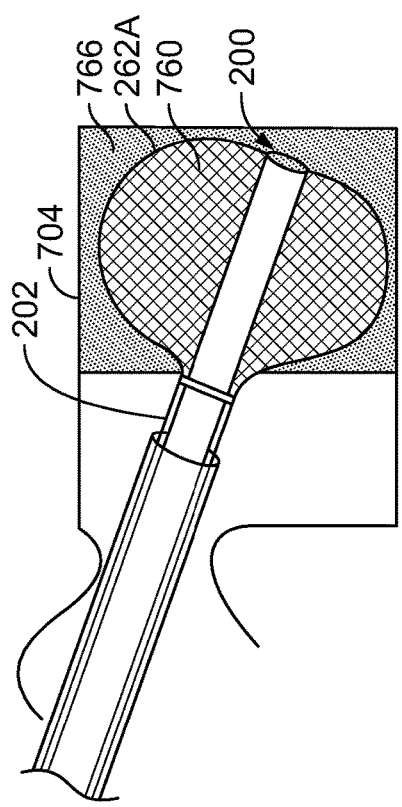
FIG. 12C illustrates an example kyphoplasty procedure with the multi-functionality head of FIG. 12A.
Figure 12D:
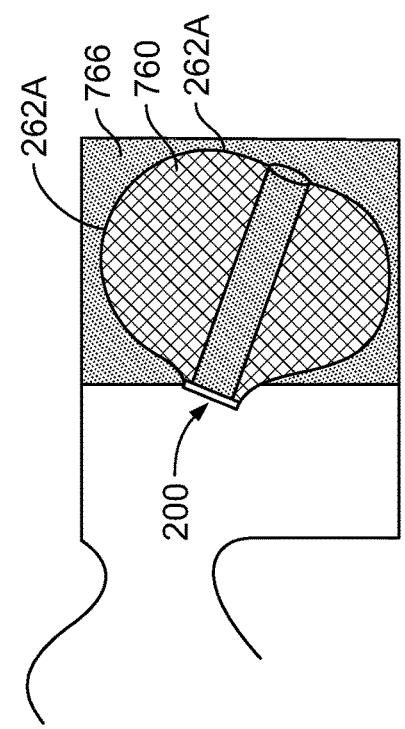
FIG. 12D illustrates an example kyphoplasty procedure with the multi-functionality head of FIG. 12A.

Referring to FIGS. 12A-12D, 13A-13D, 14A-14D, and 15A-15D, the kyphoplasty apparatus 110 can have various configurations. FIGS. 12A-12D illustrate an example configuration of the kyphoplasty apparatus 110 that includes a single multi-functionality head 200 with a spherical balloon (or similar shape) when inflated. As described herein, a multi-functionality head 200 with a deflated balloon device 262A is inserted into a vertebral body 704 (FIG. 12A), and a balloon inflation fluid 760 is delivered through a shaft 202 and inflates the balloon device 262A to the spherical shape, thereby restoring the vertebral body 704 to a desired height H2 (FIG. 12B). Once the balloon is inflated to a desired shape, a bone filler 766 is delivered through the shaft 202 and into the vertebral body 704 to fill the restored space of the vertebral body 704 (FIG. 12C). Then, the shaft 202 is decoupled from the multi-functionality head 200 and withdrawn from the vertebral body 704 (FIG. 12D).

Figure 13A:
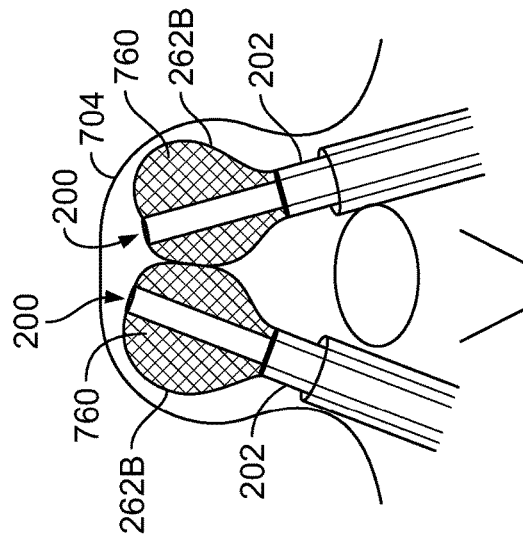
FIG. 13A illustrates an example kyphoplasty procedure that includes a set of multi-functionality heads with a spherical inflated balloon.
Figure 13B:
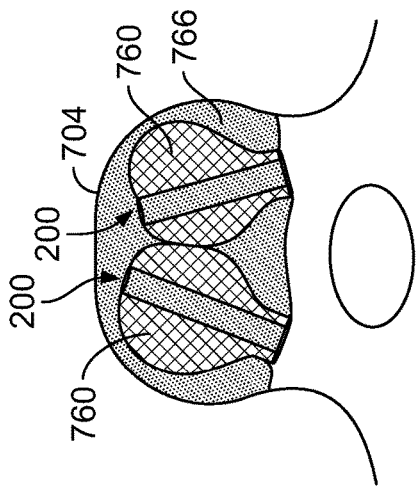
FIG. 13B illustrates an example kyphoplasty procedure with the multi-functionality head of FIG. 13A.
Figure 13C:
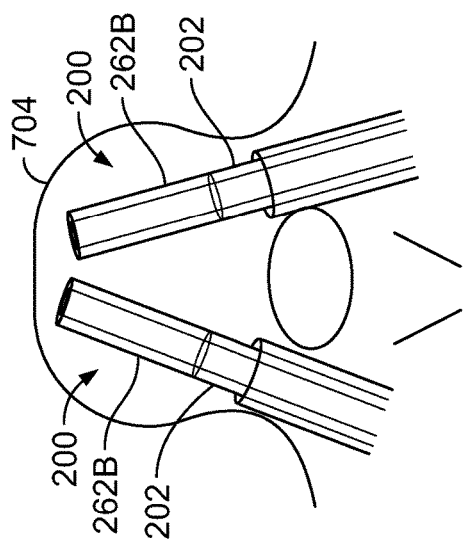
FIG. 13C illustrates an example kyphoplasty procedure with the multi-functionality head of FIG. 13A.
Figure 13D:
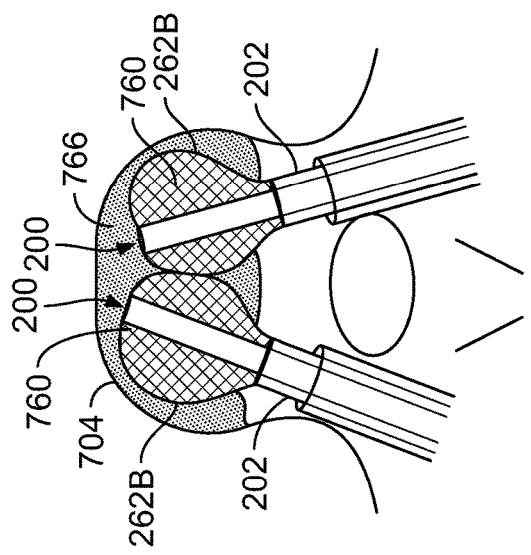
FIG. 13D illustrates an example kyphoplasty procedure with the multi-functionality head of FIG. 13A.

FIGS. 13A-13D illustrate another example configuration of the kyphoplasty apparatus 110 that includes a set of multi-functionality heads 200 with a spherical balloon (or similar shape) when inflated. As described herein, a set of multi-functionality heads 200 with deflated balloon devices 262B is inserted into a vertebral body 704 (FIG. 13A), and a balloon inflation fluid 760 is delivered through the shafts 202 and inflates the balloon devices 262B to the spherical shape, thereby restoring the vertebral body 704 to a desired height (FIG. 13B). The balloon devices 262B can be simultaneously inflated, or inflated with time shift. Once the balloons are inflated to a desired shape, a bone filler 766 is delivered through the shafts 202 and into the vertebral body 704 to fill the restored space of the vertebral body 704 (FIG. 13C). The bone fillers 766 can be simultaneously supplied, or supplied with time shift. Then, the shafts 202 are decoupled from the multi-functionality heads 200 and withdrawn from the vertebral body 704 (FIG. 13D).

FIGS. 14A-14D illustrate an example configuration of the kyphoplasty apparatus 110 that includes a single multi-functionality head 200 with a cubic balloon (or similar shape) when inflated. As described herein, a multi-functionality head 200 with a deflated balloon device 262C is inserted into a vertebral body 704 (FIG. 14A), and a balloon inflation fluid 760 is delivered through a shaft 202 and inflates the balloon device 262C to the cubic shape, thereby restoring the vertebral body 704 to a desired height H2 (FIG. 14B). Once the balloon is inflated to a desired shape, a bone filler 766 is delivered through the shaft 202 and into the vertebral body 704 to fill the restored space of the vertebral body 704 (FIG. 14C). Then, the shaft 202 is decoupled from the multi-functionality head 200 and withdrawn from the vertebral body 704 (FIG. 14D).

Figure 15A:
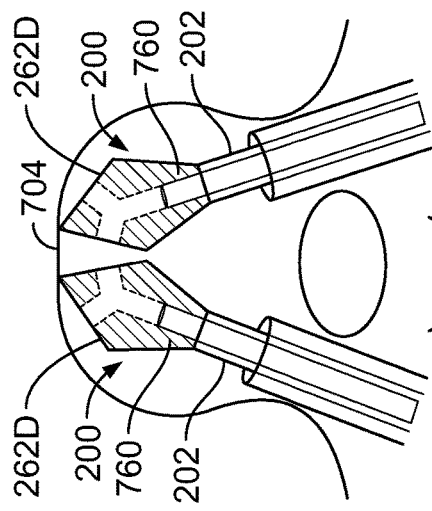
FIG. 15A illustrates an example kyphoplasty procedure includes a set of multi-functionality heads with a prism or diamond inflated balloon.
Figure 15B:
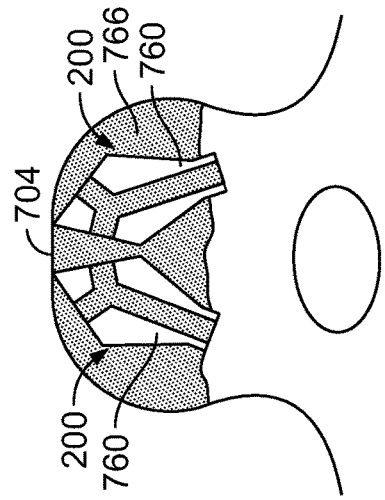
FIG. 15B illustrates an example kyphoplasty procedure with the multi-functionality head of FIG. 15A.
Figure 15C:
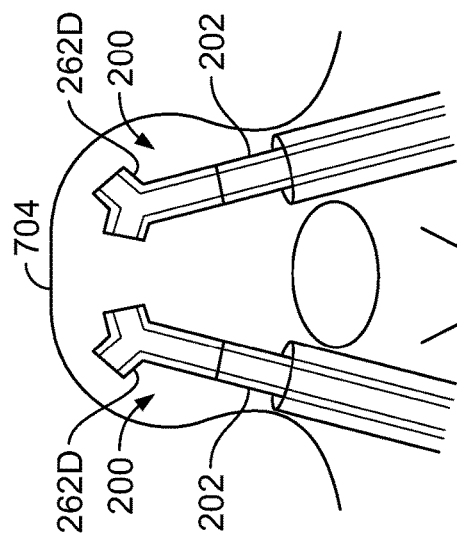
FIG. 15C illustrates an example kyphoplasty procedure with the multi-functionality head of FIG. 15A.
Figure 15D:
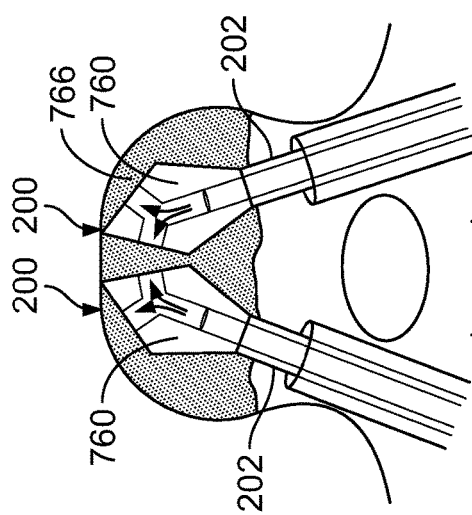
FIG. 15D illustrates an example kyphoplasty procedure with the multi-functionality head of FIG. 15A.

FIGS. 15A-15D illustrate another example configuration of the kyphoplasty apparatus 110 that includes a set of multi-functionality heads 200 with a prism or diamond balloon (or similar shape) when inflated. As described herein, a set of multi-functionality heads 200 with deflated balloon devices 262D is inserted into a vertebral body 704 (FIG. 15A), and a balloon inflation fluid 760 is delivered through the shafts 202 and inflates the balloon devices 262D to the prism or diamond shape, thereby restoring the vertebral body 704 to a desired height (FIG. 15B). The balloon devices 262D can be simultaneously inflated, or inflated with time shift. Once the balloons are inflated to a desired shape, a bone filler 766 is delivered through the shafts 202 and into the vertebral body 704 to fill the restored space of the vertebral body 704 (FIG. 15C). The bone fillers 766 can be simultaneously supplied, or supplied with time shift. Then, the shafts 202 are decoupled from the multi-functionality heads 200 and withdrawn from the vertebral body 704 (FIG. 15D).

Figure 16:
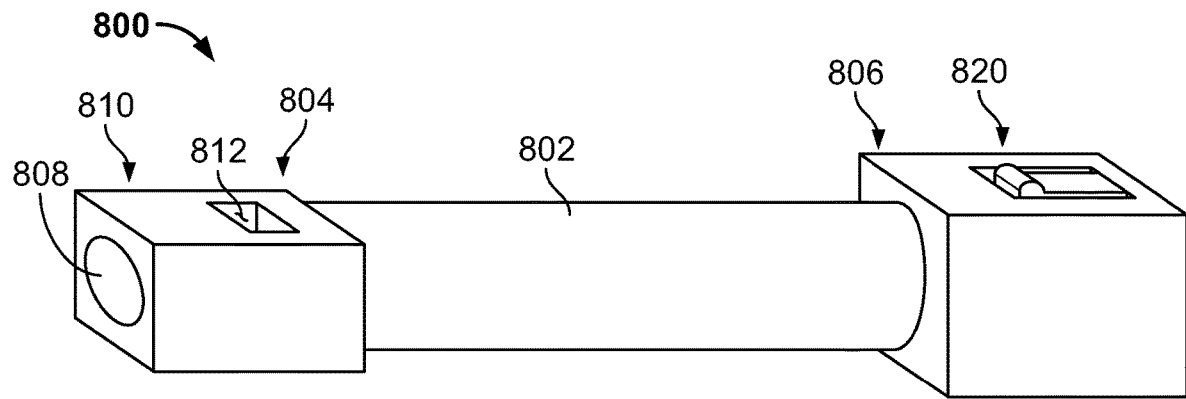
FIG. 16 illustrates an example instrument length extension device.

FIG. 16 illustrates an example instrument length extension device 800 for the connection system 600. The instrument length extension device 800 is configured to extend a length of an instrument used with the connection system 600. The instrument length extension device 800 includes an extension shaft 802 having a first end 804 and an opposite second end 806. The instrument length extension device 800 can include a first extension connector 810 mounted to the first end 804 of the extension shaft 802. In addition or alternatively, the instrument length extension device 800 can include a second extension connector 820 mounted to the second end 806 of the extension shaft 802. The instrument length extension device 800 has a channel 808 extending through a length of the device and being open at the opposite ends of the device.

The first extension connector 810 is configured identical or similar to the first connector 610 (including the first connector 710) and configured to engage with the second connector 620 (including the second connectors 720A-D) of the connection system 600. For example, the first extension connector 810 is dimensioned identically to the first connector 610 of the connection system 600, and includes a notch 812 identical to the notch 651 of the first connector 610. Similarly to the first connector 610, the first extension connector 810 can be at least partially inserted to, and coupled with, the second connector 620 of the connection system 600 that is attached to a second component (e.g., the biopsy needle 718 mounted with the first connector (FIG. 11B), the bone drill bit 740 mounted to the first connector (FIG. 11C), or the shaft 202 mounted to the first connector (FIG. 11E)). As the first extension connector 810 is coupled with the second connector 620, the second component mounting the second connector 620 is inserted through the extension shaft 802 and extends out from the other end of the extension shaft 802 (e.g., the second extension connector 820 attached to the second end 806 of the extension shaft 802).

The second extension connector 820 is configured identical or similar to the second connector 620 (including the second connectors 720A-D) and configured to engage with the first connector 610 (including the first connector 710) of the connection system 600. For example, the second extension connector 820 is dimensioned identically to the second connector 620 of the connection system 600, and includes a spring clasp 822 identical to the spring clasp 650 of the second connector 620. Similarly to the second connector 620, the second extension connector 820 can be at least partially receive and couple the first connector 610 of the connection system 600. When the first extension connector 810 and the second extension connector 820 are coupled with the second connector 620 and the first connector 610 of the connection system 600, respectively, the second component extending from the second connector 620 passes through the extension shaft 802 and continues to extend through the first component 612 (e.g., the bone introducer needle 702). As such, the instrument length extension device 800 can effectively extend a length of the first component 612 by simply coupling the second extension connector 820 of the extension device 800 to the first connector 610 of the first component 612, and by simply coupling the first extension connector 810 of the extension device 800 to the second connector 620 of the second component.

The instrument length extension device 800 can be configured to have various lengths by having different lengths of the extension shaft 802. In some implementations, the length of the instrument length extension device 800 can range from 2 cm to 20 cm. In other implementations, the length of the instrument length extension device 800 can be 10 cm.

Figure 17:
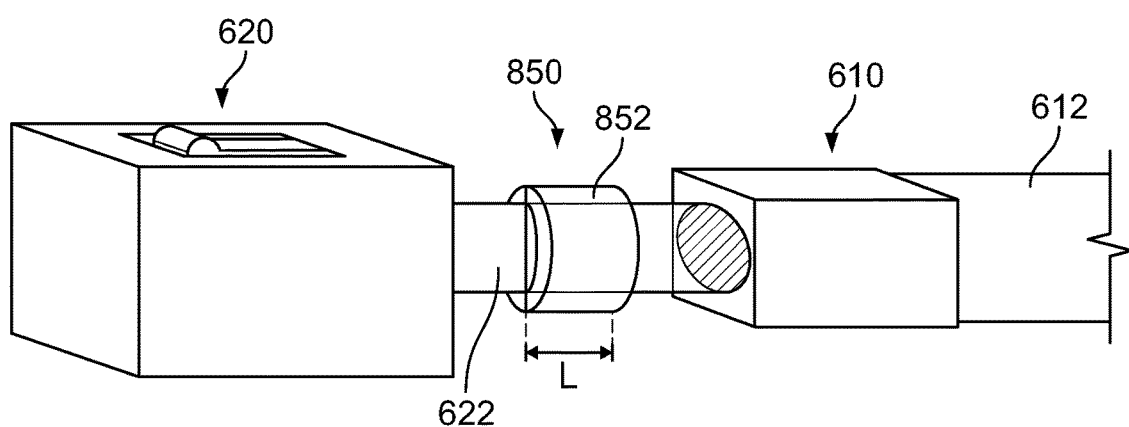
FIG. 17 illustrates an example instrument spacer.

FIG. 17 illustrates an example instrument spacer 850 for the connection system 600. The instrument spacer 850 is configured to control a length of a second component 622 being inserted through the first component 612 (e.g., the bone introducer needle 702) into a vertebral body.

The instrument spacer 850 can be configured as a sleeve 852 with a predetermined axial length L. The instrument spacer 850 can be slid around the second component 622 (e.g., a bone biopsy needle, a drill bit, etc.) before the second component 622 is inserted into the first component 612 (e.g., a bone introducer needle). The instrument spacer 850 can be slidably positioned around the second component 622 and arranged between the first connector 610 and the second connector 620. As the second component 622 moves toward a vertebral body, the instrument spacer 850 can limit an axial movement of the second component 622 relative to the first component 612. For example, the instrument spacer 850 can stop the second component 622 from moving further axially when engaging with the first connector 610 at one axial end and with the second connector 620 at the opposite axial end.

The connection system 600 can provide a set of multiple instrument spacers 850 having different axial lengths to adjust a length of the second component 622 (e.g., a drill bit) which extends out from the distal end of the first component 612 (e.g., a bone introducer needle) within a vertebral body. By way of example, where an exposed length of a drill bit is 3 cm without using a spacer, a first spacer 850 having 2 cm axial length can be used to make the exposed length of the drill bit to be 1 cm within a vertebral body, and a second spacer 850 having 1 cm axial length can be used to make the exposed length of the drill bit to be 2 cm within the vertebral body.

Referring to FIGS. 18A-18D, an example patient positioning mat 900 is described. The patient positioning mat 900 is configured to allow a patient to comfortably lie flat and prone during kyphoplasty and other procedures which require patients to remain in a prone position. The positioning mat 900 is configured to be placed on any suitable type of existing tables and beds.

The positioning mat 900 can be configured to be foldable for convenient storage and transportation between different rooms. For example, the positioning mat 900 has a plurality of sections 906 connected at folding lines 908 along which the sections 906 can be folded. The positioning mat 900 can be made of a deformable material to conform the patient's body in a prone position. In addition or alternatively, the positioning mat 900 can be made of a lightweight material to make it portable.

The positioning mat 900 includes a body portion 902 and a head portion 904 connected to the body portion 902. The body portion 902 is configured to support at least a portion of a patient's trunk (e.g., torso). The body portion 902 can be configured to further support lower limbs (e.g., legs) of the patient. The body portion 902 can be shaped to ergonomically support the body. For example, the body portion 902 can have a curved portion 922 arranged to support a desired portion of the patient's body in a prone position.

The head portion 904 extends from the body portion 902 and is configured to support a patient's head. The head portion 904 includes a rim portion 910 that at least partially defines an opening 912 for exposing at least a portion of the patient's face (including eyes, nose, and mouth) while supporting the patient's head when the patient lies in a face-down position. The head portion 904 includes a vertical support portion 914 configured to position the rim portion 910 away from a bottom level G (e.g., a table or bed surface) on which the positioning mat 900 is set. The vertical support portion 914 can provide a space between the rim portion 910 and the bottom level G so that the patient's face does not touch the bottom level G and is sufficiently raised from the bottom level G. The vertical support portion 914 can be configured to be adjustable in length. For example, the vertical support portion 914 can be configured to be telescopically expandable and retractable so that the height of the head portion 904 is adjusted.

The head portion 904 can include one or more tube notches 916 configured to route one or more tubes 918 (e.g., oxygen tubes) around the patient's head H during procedures. As illustrated in FIG. 18A, the tube notches 916 can be provided in the rim portion 910 and adjacent the opening 912. The head portion 904 includes one or more vent openings 920 provided below the rim portion 910 and configured to allow air to flow through the vent openings 920, thereby helping the patient to breath during procedures.

Figure 19A:
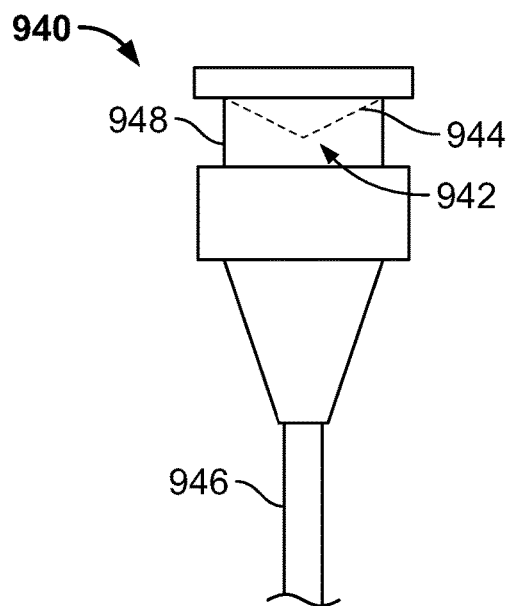
FIG. 19A is a side view of an example bone introducer needle.
Figure 19B:
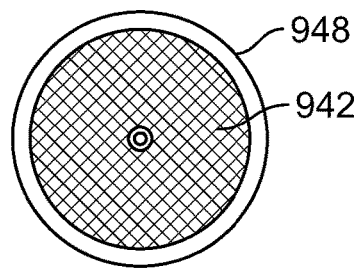
FIG. 19B is a top view of the bone introducer needle of FIG. 19A.
Figure 19C:
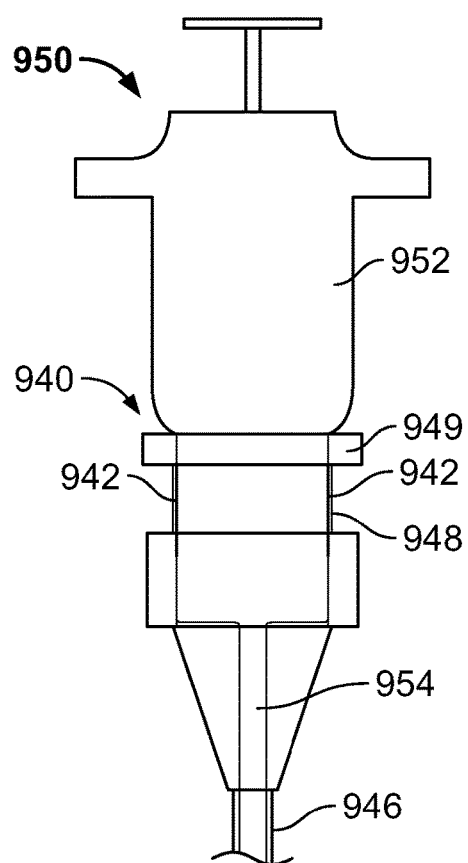
FIG. 19C is a schematic side cross sectional view of the bone introducer needle engaging an example biopsy device.

Referring to FIGS. 19A-19C, an example introducer needle 940 is described. In particular, FIG. 19A is a side view of an example introducer needle 940, and FIG. 19B is a top view of the introducer needle 940. FIG. 19C is a schematic side cross sectional view of the introducer needle 940 engaging an example biopsy device. The introducer needle 940 can be used for the bone introducer needle 702 described in FIG. 11A.

The introducer needle 940 can include a backflow prevention device 942. The backflow prevention device 942 can include a one-way valve 944 configured to prevent backflow of blood or body fluids. For example, the backflow prevention device 942 can prevent blood or body fluids from flowing in a direction away from a patient's body when an instrument (e.g., a biopsy needle, a drill, etc.) is removed from the patient's body through the introducer needle 940.

The introducer needle 940 can include a needle 946 and a hub 948 connected to an end of the needle 946. The hub 948 defines an interior space being in fluid communication with a canal of the needle 946, and further includes the backflow prevention device 942 (e.g., the one-way valve 944) arranged within the interior space of the hub 948. The one-way valve 944 can be made of a flexible material, such as silicone, rubber, etc.

As illustrated in FIG. 19C, a biopsy device 950, which can be used for soft tissue biopsy or bone biopsy, can be inserted into the introducer needle 940. When the biopsy device 950 is inserted to the introducer needle 940, a biopsy gun 952 of the biopsy device 950 is partially inserted to the hub 948 of the introducer needle 940, and a biopsy needle 954 is inserted through the needle 946 of the introducer needle 940. Further, the biopsy device 950 opens the one-way valve 944 of the introducer needle 940. As the biopsy device 950 is removed from the introducer needle 940, the one-way valve 944 is closed to prevent backflow of any fluid from the patient's body. In some implementations, the introducer needle 940 can have a size ranging between 16 gauge and 18 gauge, and the biopsy device 950 can have a size ranging between 18 gauge and 20 gauge.

In addition, the hub 948 can provides a coupling structure 949 for detachably engaging an instrument (e.g., a biopsy device, a drill, etc.). An example of the coupling structure 949 includes a luer lock, a flange, or other types of fasteners.

Figure 20:
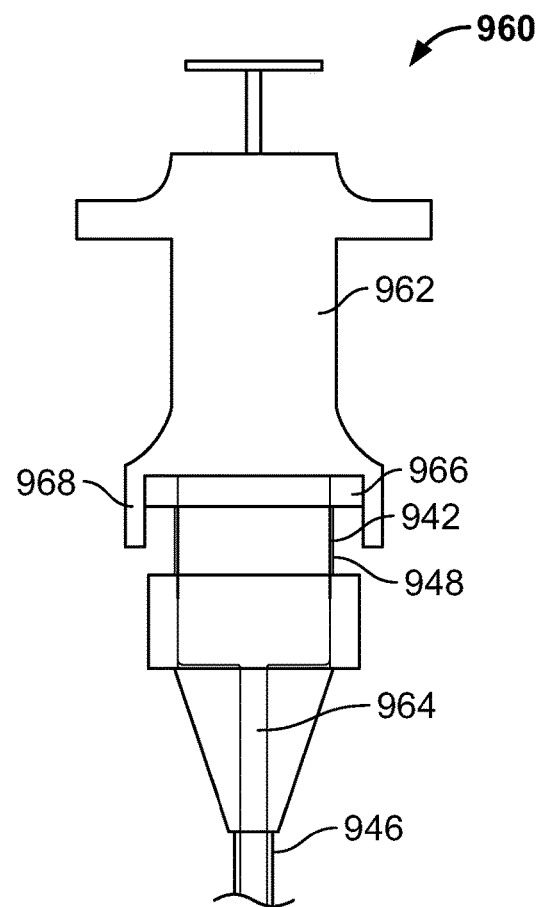
FIG. 20 is a schematic side cross sectional view of an example biopsy device.

FIG. 20 is a schematic side cross sectional view of an example biopsy device 960. The biopsy device 960 can be engageable with various types of introducer needles although it is primarily illustrated and described to be used with the introducer needle 940 of FIGS. 19A-19C.

The biopsy device 960 can be configured to be similar to the biopsy device 950 except for a locking feature. Similarly to the biopsy device 950, the biopsy device 960 includes a biopsy gun 962 and a biopsy needle 964. The biopsy device 960 is configured to be coupled with an introducer needle without an additional locking device. For example, as illustrated in FIG. 20, the introducer needle 940 includes the hub 948 with a female luer lock connector 966, and the biopsy gun 962 of the biopsy device 960 includes a male luer lock connector 968. As the biopsy device 960 is at least partially inserted into the hub 948 of the introducer needle 940, the male luer lock connector 968 of the biopsy device 960 can be engaged with the female luer lock connector 966 of the hub 948, thereby securing the biopsy gun 962 to the hub 948 of the introducer needle 940 without a separate luer lock ring or other additional elements. The male luer lock connector 968 can be formed integrally with the biopsy gun 962. Alternatively, the male luer lock connector 968 can be made separately and fixed to the biopsy gun 962.

Referring to FIGS. 21-24, 25A-25C, and 26A-26C, an example radiation-free interventional spinal training system 1000 is described.

FIG. 21 is a schematic perspective view of an example interventional spinal training system 1000, which can be used in a training environment 104 as illustrated in FIG. 1. FIG. 22 is a side cross sectional view of the training system 1000 of FIG. 21, and FIG. 23 is a top view of the training system 1000 of FIG. 1. The training system 1000 can be configured for kyphoplasty and other interventional procedures. The training system 1000 can include one or more individual vertebral body models 1002, a spinal canal model 1004, and a patient body model 1008.

Figure 25A:
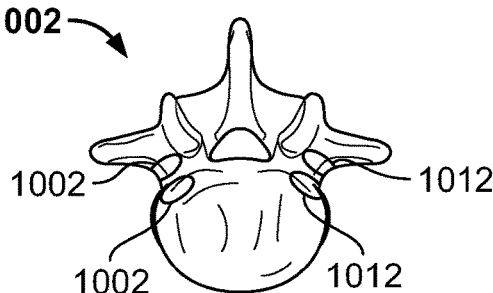
FIG. 25A is a schematic top view of an example vertebral body model.
Figure 25B:
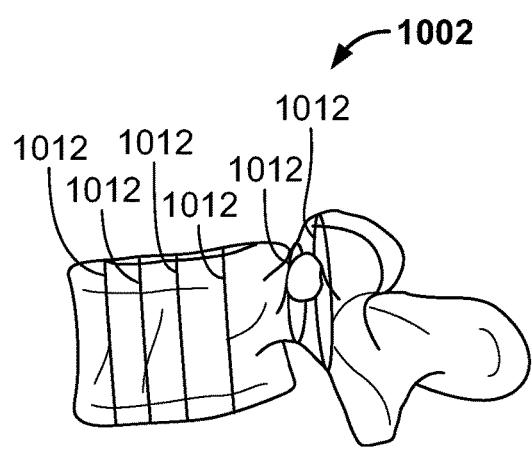
FIG. 25B is a schematic side view of the vertebral body model of FIG. 25A.
Figure 25C:
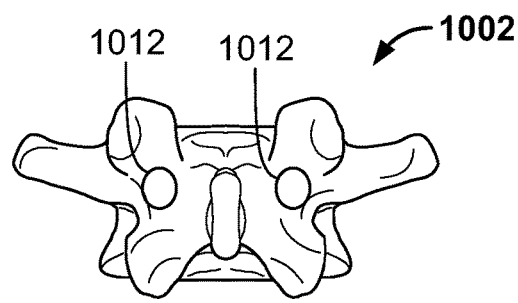
FIG. 25C is a schematic bottom view of the vertebral body model of FIG. 25A.

The vertebral body models 1002 (e.g., chunks, blocks, pieces, etc.) can be configured to simulate vertebral bodies, as illustrated in FIG. 25A-25C. The vertebral body models 1002 can be made similarly to the shape and/or size of actual vertebral bodies. Other outer shapes, such as sphere, cones, cylinders, cubes, rectangular prisms, and other prisms, are also possible. The vertebral body models 1002 can be made of a material that is penetrable by needles, such as silicone. The vertebral body models 1002 can be made to be transparent so as to visualize instruments, elements, and substances inserted into the models, such as kyphoplasty needles, balloons, balloon fluids, and bone fillers inside the models. In addition or alternatively, the vertebral body models 1002 can be configured to make an outside part (e.g., crust) harder than an inside part, thereby simulating tactile experience of touching needles to spinal bones.

As illustrated in FIG. 25A-25C, the vertebral body models 1002 can include markers 1012 indicative of educational anatomic landmarks to facilitate correct needle placement. Example shapes of markers can include lines, dots, circles, symbols, and other suitable objects. The markers 1012 can be provided to the vertebral body models 1002 in various manners. For example, the markers 1010 can be engraved and/or painted on the vertebral body models 1002.

Figure 24:
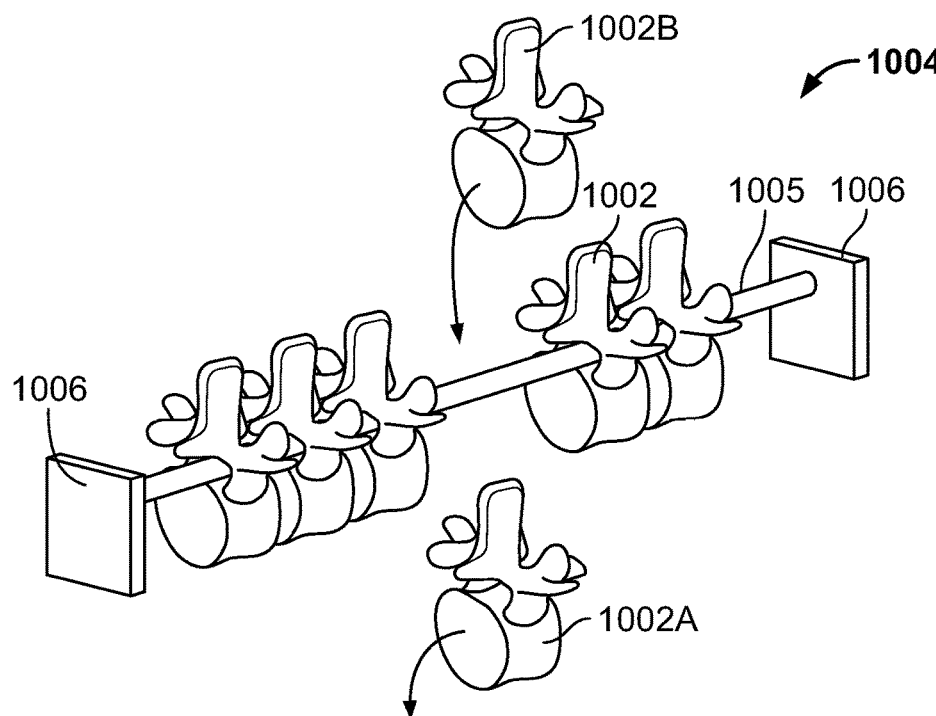
FIG. 24 is a schematic perspective view of an example spinal canal model with example vertebral body models.

Referring also to FIG. 24, the training system 1000 can include a spinal canal model 1004 configured to connect the vertebral body models 1002, thereby simulating a spinal canal with vertebral bodies. The spinal canal model 1004 can include a rod 1005 configured to engage a series of vertebral body models 1002. The spinal canal model 1004 can be configured to allow the vertebral body models 1002 to be individually engaged with and removed from the spinal canal model 1004. Each of the vertebral body models 1002 can be replaced if damaged during simulated procedure. For example, a damaged vertebral body 1002A is removed from the spinal canal model 1004 and a new vertebral body 1002B is engaged with the spinal canal model 1004 to replace the removed vertebral body 1002A.

The spinal canal model 1004 can be configured to rest on a table top or other surface in the training environment 104. For example, the spinal canal model 1004 includes stands 1006 mounted to the opposite ends of the spinal canal model and configured to be seated on a surface to support the vertebral body models 1002 above the surface. The spinal canal model 1004 can be made of a transparent material to allow visualization of bone needles inside a vertebral bone.

Referring to FIGS. 21-23, the training system 1000 can include a patient body model 1008 that simulates a patient body. The patient body model 1008 can be made of a transparent material (e.g., silicone) to allow visualization of needles approaching the vertebral body models 1002. The patient body model 1008 can be configured to be placed over the spinal canal model 1004 engaging one or more vertebral body models 1002, and rest on the rest top on which the spinal canal model 1004 also rests. For example, the patient body model 1008 can include a tunnel 1009 to receive the spinal canal model 1004 engaging one or more vertebral body models 1002. The patient body model 1008 can be of various shapes, such as a half-cylindrical outer shape. The patient body model 1008 can have a flat bottom configured to rest on a surface, as illustrated in FIG. 21. The patient body model 1008 can be made of a material that is penetrable by needles and provides tactile simulation of advancing needles through paraspinal soft tissues.

Figure 26A:
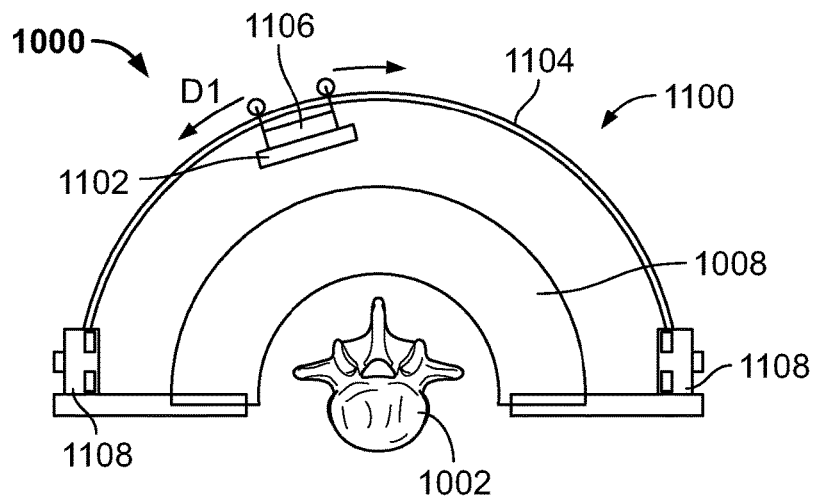
FIG. 26A is a schematic front view of the interventional spinal training system with an example image capturing system.
Figure 26B:
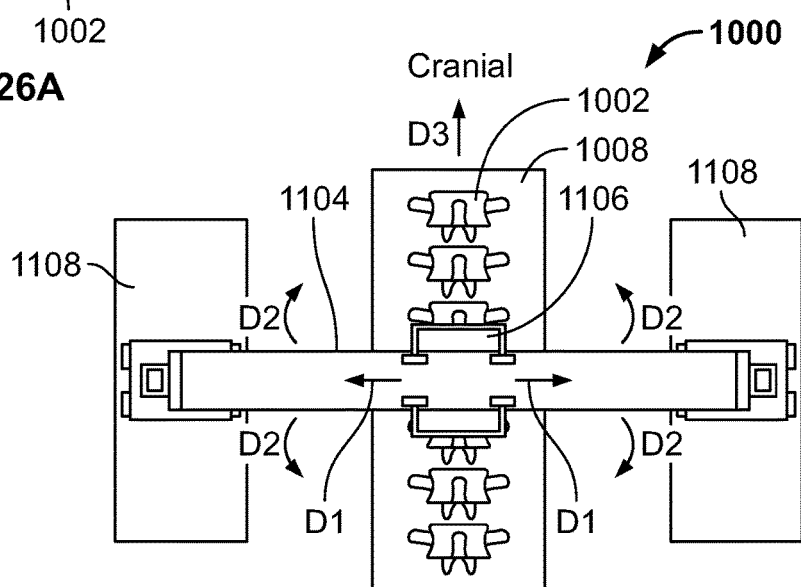
FIG. 26B is a schematic top view of the interventional spinal training system of FIG. 26A.
Figure 26C:
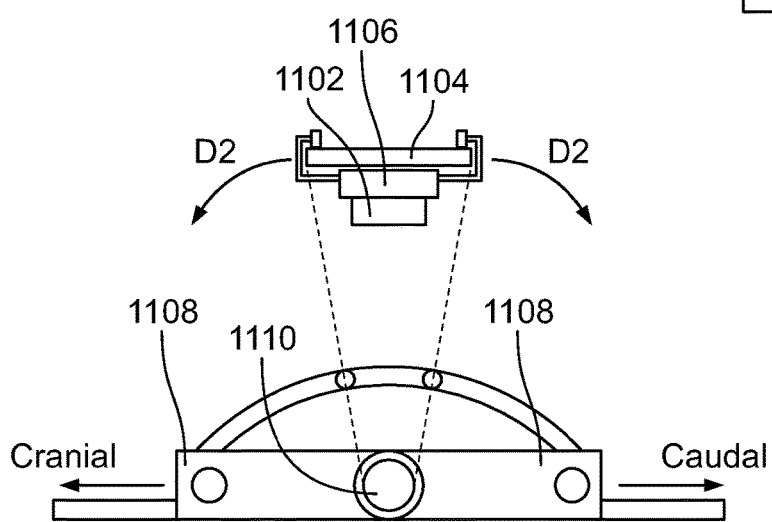
FIG. 26C is a schematic side view of the interventional spinal training system of FIG. 26A.

Referring to FIGS. 26A-26C, the training system 1000 can include a camera support device 1100 configured to simulate a C-arm machine of kyphoplasty or other procedures. The camera support device 1100 is configured to movably support an image capturing device 1102 with respect to the patient body model 1008 and/or the spinal canal model 1004 engaging with the vertebral body models 1002.

The camera support device 1100 can include a rail frame 1104 extending around the patient body model 1008. The rail frame 1104 can be shaped to be arc around the patient body model 1008. Other shapes of the rail frame 1104 are also possible, such as rectangle, square, etc. The rail frame 1104 can be supported by bases 1108 mounted to the ends of the rail frame 1104. The bases 1108 can be configured to rest on a surface, such as a table top.

The camera support device 1100 can include a camera bracket 1106 slidably engaged with the rail frame 1104 and configured to mount an image capturing device 1102 capable of capturing videos and/or still images. Examples of the image capturing device 1102 include a digital camera, a mobile device (e.g., a smartphone, a tablet, etc.) including a digital camera, and other image capturing devices.

The camera bracket 1106 is configured to slide along the rail frame 1104 (e.g., along a direction D1) above the patient body model 1008 while capturing images (e.g., still images and/or video images) of training procedures with the patient body model 1008, the spinal canal model 1004, and/or the vertebral body models 1002. The images taken by the image capturing device 1102 can be transmitted to a display device (e.g., the display device 182 in FIG. 1) and displayed on the display device so that users (e.g., trainers and trainees T in FIG. 1) can watch the procedures in real-time as they perform the procedures, just as physicians (e.g., the physician P in FIG. 1) can monitor a surgical site (e.g., the inside of a vertebral body) through a C-arm system (e.g., the image scanner 180 in FIG. 1) during the procedure (e.g., in the surgical theater 102).

Referring to FIG. 24C, the rail frame 1104 of the camera support device 1100 can be configured to be pivotable in a cranial-caudal plane (along a direction D2), just as a C-arm system is maneuvered during interventional spine procedures. For example, the rail frame 1104 is pivotally connected to the bases 1108 so as to rotate around a pivot axis 1110.

Referring to FIG. 26B, the camera support device 1100 can be configured to be movable along a cranial-caudal direction (e.g., a direction D3). For example, the bases 1108 can be configured to move along the direction D3 so that the rail frame 1104 mounting the image capturing device 1102 is entirely moved along the direction D3. Alternatively, the bases 1108 and the rail frame 1104 coupled thereto can remain stationary, and the spinal canal model 1004 (including the vertebral body models 1002) and/or the patient body model 1008 can be moved relative to the camera support device 1100 in the direction D3.

The camera support device 1100 can be manually and/or remotely controlled to move in different planes of movement. For example, the camera bracket 1106 can be manually moved along the rail frame 1104, and/or the rail frame 1104 can be manually pivoted relative to the bases 1108. Alternatively or in addition, the camera bracket 1106 and/or the rail frame 1104 are connected to a controller that provides a user interface (e.g., buttons, joysticks, etc.), and a user can control the movements of the camera bracket 1106 and/or the rail frame 1104 using the user interface. The controller can be of various types, such as a remote controller or a software program (e.g., a mobile application) running on a remote computing device. The camera support device 1100 can be connected to the controller using wireless and/or wired communications interface.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A method for a kyphoplasty procedure, the method comprising:
    inserting a balloon implant into a vertebral body while a central implant shaft of the balloon implant is releasably connected to a distal end of a delivery shaft;
    while a balloon device of the balloon implant is mounted along the central implant shaft and is positioned in the vertebral body, inflating the balloon device of the balloon implant to an inflated configuration by delivering a balloon fluid through a balloon inflation port along the central implant shaft and into an interior of the balloon device;
    while the balloon device is in the inflated configuration in the vertebral body, injecting a bone filler to the vertebral body via the central implant shaft that extends to an output port positioned distally of the balloon device such that a balloon wall of the balloon device simultaneously engages with the balloon fluid along the interior of the balloon device and with the bone filler along an exterior of the balloon device;
    after injecting the bone filler to the vertebral body and distally of the balloon device, disconnecting the delivery shaft from the balloon implant; and
    removing the delivery shaft from the vertebral body.

2. The method of claim 1, further comprising:
    prior to inserting the balloon implant into the vertebral body, inserting a bone introducer needle into the vertebral body, wherein the balloon implant is inserted into the vertebral body through the bone introducer needle.

3. The method of claim 1, further comprising:
    prior to inserting the balloon implant into the vertebral body, inserting a bone introducer needle with an inner stylette toward an anterior aspect of the vertebral body using image guidance;
    removing the inner stylette from the bone introducer needle;
    coaxially inserting the delivery shaft releasably coupled with the balloon implant into the bone introducer needle; and
    retracting posteriorly the bone introducer needle over the delivery shaft with the coupled balloon implant such that the balloon implant is positioned at least partially uncovered inside the vertebral body.

4. The method of claim 3, further comprising:
    inserting a bone biopsy needle into the vertebral body;
    controlling the bone biopsy needle to remove a bone sample; and
    removing the bone biopsy needle from the vertebral body.

5. The method of claim 3, further comprising:
    inserting a bone drill bit into the vertebral body;
    controlling the bone drill bit to create a cavity in the vertebral body; and
    removing the bone drill bit from the vertebral body.

6. The method of claim 5, further comprising:
    inserting a cavity curette into the vertebral body;
    controlling the cavity curette to remove debris in the cavity; and
    removing the cavity curette from the vertebral body.

7. The method of claim 3, wherein the balloon implant includes a spring-biased footplate configured to be pressed against an inner surface of the bone introducer needle.

8. The method of claim 1, wherein the balloon device is attached to an exterior surface of, and positioned coaxial with, the central implant shaft of the balloon implant.

9. The method of claim 1, wherein the balloon implant comprises:
    a first valve disposed in a first conduit and configured to prevent a backflow of the balloon fluid.

10. The method of claim 1, wherein the balloon implant comprises:
    a balloon port valve configured to selectively open and close the balloon inflation port and prevent a backflow of the balloon fluid through the balloon inflation port.

11. The method of claim 1, wherein the central implant shaft of the balloon implant comprises:
    a first conduit and a second conduit.

12. The method of claim 11, wherein the delivery shaft has a distal end, a proximate end, a bone filler channel, and a balloon fluid channel,
    wherein the bone filler channel is configured to be in fluid communication with the second conduit of the balloon implant and deliver the bone filler into the vertebral body through the second conduit,
    wherein the balloon fluid channel is configured to be in fluid communication with the first conduit of the balloon implant and deliver the balloon fluid into the balloon device through the first conduit to inflate the balloon device within the vertebral body.

13. The method of claim 11, wherein the central implant shaft is configured to snap-fit the distal end of the delivery shaft.

14. The method of claim 11, wherein the second conduit extends through a length of the central implant shaft, and the first conduit is arranged around the second conduit.

15. The method of claim 11, wherein the balloon device is attached to an exterior surface of, and positioned coaxial with, the central implant shaft.

16. The method of claim 12, wherein the balloon fluid channel is arranged around the bone filler channel.

17. The method of claim 12, wherein the proximate end of the delivery shaft is configured to fluidly connect to a bone filler source and a balloon fluid source, the bone filler source configured to be in fluid communication with the bone filler channel, and the balloon fluid source configured to be in fluid communication with the balloon fluid channel.

18. The method of claim 11, wherein the balloon implant further comprises:

a first valve disposed in the first conduit and configured to prevent a backflow of the balloon fluid, wherein the first valve is a conical one-way valve.

19. The method of claim 11, wherein the balloon implant further comprises:

the balloon inflation port configured to provide fluid communication between the first conduit and the balloon device; and a balloon port valve configured to selectively open and close the balloon inflation port and prevent a backflow of the balloon fluid through the balloon inflation port, wherein the balloon port valve includes at least one of a one-way flap valve or a one-way sleeve valve.

20. The method of claim 7, wherein the footplate has a free end configured to be pressed against the inner surface of the bone introducer needle when the bone introducer needle partially surrounds the balloon implant, and further configured to be flexed back when the bone introducer needle is pulled back.

* * * * *